(12) United States Patent
Reich et al.

(10) Patent No.: US 7,521,431 B2
(45) Date of Patent: Apr. 21, 2009

(54) COMPOSITIONS AND METHODS FOR SIRNA INHIBITION OF HIF-1 ALPHA

(75) Inventors: Samuel Jotham Reich, Bala Cynwyd, PA (US); Enrico Maria Surace, Milan (IT); Michael J. Tolentino, Villanova, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 516 days.

(21) Appl. No.: 10/699,557

(22) Filed: Oct. 31, 2003

(65) Prior Publication Data

US 2004/0180357 A1 Sep. 16, 2004

Related U.S. Application Data

(60) Provisional application No. 60/423,262, filed on Nov. 1, 2002.

(51) Int. Cl.
*C07H 21/02* (2006.01)
*C07H 21/04* (2006.01)
*A61K 31/70* (2006.01)
*C12N 5/00* (2006.01)
*C12Q 1/68* (2006.01)

(52) U.S. Cl. ............... 514/44; 435/6; 435/375; 435/377; 435/320.1; 536/23.1; 536/24.1; 536/24.5

(58) Field of Classification Search ............ None
See application file for complete search history.

(56) References Cited

U.S. PATENT DOCUMENTS

| | | | | |
|---|---|---|---|---|
| 5,624,803 | A | * | 4/1997 | Noonberg et al. ............ 435/6 |
| 5,801,156 | A | * | 9/1998 | Robinson et al. ............ 514/44 |
| 6,020,462 | A | | 2/2000 | Semenza |
| 6,177,401 | B1 | | 1/2001 | Ullrich et al. |
| 6,506,559 | B1 | | 1/2003 | Fire et al. |
| 2002/0086356 | A1 | | 7/2002 | Tuschl et al. |
| 2002/0132788 | A1 | | 9/2002 | Lewis et al. |
| 2002/0162126 | A1 | | 10/2002 | Beach et al. |
| 2002/0173478 | A1 | | 11/2002 | Gewirtz |
| 2004/0096848 | A1 * | | 5/2004 | Thrue et al. ............ 435/6 |
| 2004/0259247 | A1 * | | 12/2004 | Tuschl et al. ............ 435/375 |

FOREIGN PATENT DOCUMENTS

CA 2359180 8/2000

OTHER PUBLICATIONS

Bennett et al., *Hum Gene Ther* 10:1763-1769 (abstract) (Sep. 1996).
Elbashir et al., *Nature*, 411:494-498 (May 24, 2001).
Elbashir et al., *Genes& Development* 15:188-200 (2001).
Erickson, D., "RNAi Revs Up", *Start-Up* (A#2002900168) pp. 1-12 (Oct. 2002).
Fire et al., *Nature*, 391:806-811 (Feb. 19, 1998).
Hoeg et al., "In vitro and in vivo Efficacy of a HIF-1alpha-antisense oligonucleotide containing locked nucleic acids", *ECJ Supplements*, pp. S212-S213 (Sep. 2003) (*abstract only*).
Holash et al., *PNAS*, 99(17) 11393-11398 (Aug. 20, 2002).
Kang et al., "An Antisense Oligonucleotide that Inhibits the Expression of Hypoxia-Inducible Factor-1alpha Alters Hypoxia-Induced Changes in Proliferation and viability of Human Cardiac Fibroblasts", p. II, 57 (*abstract only*).
Kim et al., *PNAS*, 99(17):11399-11404. (Aug. 20, 2002).
Novina et al., *Nature Medicine*, 8(7):81-686 (Jul. 2002).
Sun et al., "Gene Transfer of Antisense Hypoxia Inducible Factor-1 alpha Enhances the therapeutic Efficacy of Cancer Immunotherapy", *Gene Therapy*, 8:638-645 (2001).
Tischer et al., *J. Biol Chem* 266:11947-11954 (abstract) (Jun. 25, 1991).
Tuschl, T., The siRNA user guide (revised Oct. 11, 2002), Accessed from http://www.mpibpc.gwdg.de/abteilungen/100/105/sirna.html. on Nov. 1, 2002.
Tuschl, T., *Nat. Biotech* 20: 446-448 (May 2002).
Van Brunt, J., *Signals Magazine*: "Buzz—Shoot the Messenger" Aug. 22, 2002, Accessed from http://www.signalsmag.com/signalsmag..../3DF5AEF6049CC81C99256C1D0055BAA on Oct. 28, 2002.
Wu et al., *Mol Cell Biol*, vol. 22:22: 7758-7768 (abstract) (Nov. 2002).
Xia et al., *Nature Biotechnology*, vol. 20:1006-1010 (Oct. 2002).
Krishnamachary et al., Regulation of Colon Carcinoma Cell Invasion by Hypoxia-Inducible Factor 1[1], Cancer Res. 63:1138-1143.

* cited by examiner

*Primary Examiner*—Sean R McGarry
(74) *Attorney, Agent, or Firm*—Pepper Hamilton LLP

(57) ABSTRACT

RNA interference using small interfering RNAs which target HIF-1 alpha mRNA inhibit expression of the HIF-1 alpha gene. As HIF-1 alpha is a transcriptional regulator of VEGF, expression of VEGF is also inhibited. Control of VEGF production through siRNA-mediated down-regulation of HIF-1 alpha can be used to inhibit angiogenesis, in particularly in diseases such as diabetic retinopathy, age related macular degeneration and many types of cancer.

39 Claims, 3 Drawing Sheets

US 7,521,431 B2

SEQUENCE LISTING

<160> NUMBER OF SEQ ID NOS: 299

<210> SEQ ID NO 1
<211> LENGTH: 2964
<212> TYPE: DNA
<213> ORGANISM: Homo sapiens

<400> SEQUENCE: 1

```
ggccgtccct ggcggcggag atggcggcga cagcggcgga ggctgtgacc tctggctctg      60
gagagccccg ggaggaggct ggagccctcg gccccgcctg gcatgaatcc cagttgcgca     120
gttatagctt cccgactagg cccattccgc gtctgagtca gagcgacccc cgggcagagg     180
agcttattga gaatgaggag cctgtggtgc tgaccgacac aaatcttgtg tatcctgccc     240
tgaaatggga ccttgaatac ctgcaagaga atattggcaa tggagacttc tctgtgtaca     300
gtgccagcac ccacaagttc ttgtactatg atgagaagaa gatggccaat ttccagaact     360
ttaagccgag gtccaacagg gaagaaatga atttcatga gttcgttgag aaactgcagg     420
atatacagca gcgaggaggg gaagagaggt tgtatctgca gcaaacgctc aatgacactg     480
tgggcgggaa gattgtcatg gacttcttag gttttaactg gaactggatt aataagcaac     540
agggaaagcg tggctggggg cagcttacct ctaacctgct gctcattggc atggaaggaa     600
atgtgacacc tgctcactat gatgagcagc agaactttt tgctcagata aaaggttaca     660
aacgatgcat cttattccct ccggatcagt tcgagtgcct ctacccatac cctgttcatc     720
acccatgtga cagacagagc caggtggact ttgacaatcc cgactacgag aggttcccta     780
atttccaaaa tgtggttggt tacgaaacag tggttggccc tggtgatgtt ctttacatcc     840
caatgtactg gtggcatcac atagagtcat tactaaatgg ggggattacc atcactgtga     900
acttctggta taagggggct cccacccta agagaattga atatcctctc aaagctcatc     960
agaaagtggc cataatgaga aacattgaga agatgcttgg agaggccttg gggaacccac    1020
aagaggtggg gcccttgttg aacacaatga tcaagggccg gtacaactag cctgccaggg    1080
gtcaaggcct cctgccaggt gactgctatc ccgtccacac cgcttcattg atgaggacag    1140
gagactccaa gcgctagtat tgcacgctgc acttaatgga ctggactctt gccatggccc    1200
aggagtcagg tgtttggagc gaggcagggc agttggcact ccactcctat ttggagggac    1260
```

-continued

```
ttcataccct tgcctcttgt gccccagcac cttctctctc tgcccccccgc ctaaagtcct    1320 gcattcagtg tgtggagtcc cagcttttgg ttgtcatcat gtctgtgtgt atgttagtct    1380
gtcaacttcg gaatgtgtgc gtgtgtgtgc atgcacacgc atgtatgtat ctgttccctg    1440
ttccttctgg gtcaggctgt cacttccggc tctcggccct atctcctgca acctcagtgc    1500
ctcagcctga gagagagatg agatgctctt ggactcccca ctgcatctgg gctgcagggc    1560
cagagctagt ctgaccatta ggtcagtctg cctcctgaca gttttgcgt agtcaagctc    1620 taggcggtat gggaatggct accgggactc taatggggtg aaagagaggg gaggcttgcc    1680
tttgagagcc tatatagcct tcctgtgaga aggattaga tagggttcca actgggccta    1740
caagctcaag ccatacataa aaggaccttg ggacataaga accaatgatt gtgcataagt    1800
tctaaattag agacacatat agtttctctc tttcagcacc agctcttgcc cctatgctgg    1860
gtaccaaggg agttctccta gctgtggctt ctctaggttc taggggtgca agcctctgtg    1920
tgtttgtttg tgtgtgtctg tgtgtgcgta tccacactag gggtgcaagc ctctgggtgt    1980
gtgtgtgtgt gtgcgtgcgt gtgtgtgtgt gtgtccgtgt gtgtgtgtgt gtgtccacac    2040
tggccagcct ccctacttac caaggttctc cactgcttac cttttccagt gggacagtac    2100
agtgtgagcc cccgggaagt actgcctgac ctatcctaag cttttacact tggattttag    2160
ccatcatatg ttggccaggt ttcactgcag cctgcccgag gctaactggc tagagcctcc    2220
aggccctatg atgctccctg cccaggccat atccttatt cctgctgagc ttcctggctg    2280
aatagatgaa atggggtcaa gcccaggcag ctcattcact atctgtgatc cacctcaggg    2340
cacgggcaaa cacataggct tgcgtcttaa agccagctcc tctgccagac cccgttgtaa    2400
tgtgccacaa caccctcaat agtcaggca actggtggag catggaagtc gaatttccttt   2460 ttctgttagg agctactcct gggaacccct ctcagggctg cagcttacag gtgggcagct    2520
gtgattgcac aacttgaagg gccatcattc acatctattc agtgggagtg gggtccctgg    2580
gattgggcag tgtggtggcc ctgtgtctcc tcacctctgc tcctgtcttc atcaccttct    2640
ctctggaagg gaagaggagt tggaaggtct ctggttttct tttcttttt tttttttgcc    2700 aaaggtttac ttccagcatc tgagctctgg ctctcacccc tgaagctcag ttatagtgca    2760
ctgatgaact gagaggatgc gtgtggatgt gtgtgcatgc ctgagtgcgt ttttggggga    2820
ggggtgttta tttttagtac cccattctgg ggttctctga tgcagtgtgg atgtgaagat    2880
atggtacctt ctcaagtgta gctctttcaa atatagtcaa tgctgggaaa aaaaaaaaa    2940 aaaaaaaaaa aaaaaaaaa aaaa                                            2964
```

<210> SEQ ID NO 2
<211> LENGTH: 3958
<212> TYPE: DNA
<213> ORGANISM: Homo sapiens

<400> SEQUENCE: 2

```
gtgctgcctc gtctgagggg acaggaggat caccctcttc gtcgcttcgg ccagtgtgtc      60
gggctgggcc ctgacaagcc acctgaggag aggctcggag ccgggcccgg accccggcga    120 tgccgcccg cttctctcta gtctcacgag gggtttcccg cctcgcaccc ccacctctgg     180
acttgccttt ccttctcttc tccgcgtgtg agggagccca gcgcttaggc cggagcgagc    240 ctggggccg cccgccgtga agacatcgcg gggaccgatt caccatggag ggcgccggcg    300
gcgcgaacga caagaaaaag ataagttctg aacgtcgaaa agaaaagtct cgagatgcag    360
ccagatctcg gcgaagtaaa gaatctgaag ttttttatga gcttgctcat cagttgccac    420
```

-continued

```
ttccacataa tgtgagttcg catcttgata aggcctctgt gatgaggctt accatcagct    480
atttgcgtgt gaggaaactt ctggatgctg gtgatttgga tattgaagat gacatgaaag    540
cacagatgaa ttgcttttat ttgaaagcct tggatggttt tgttatggtt ctcacagatg    600
atggtgacat gatttacatt tctgataatg tgaacaaata catgggatta actcagtttg    660
aactaactgg acacagtgtg tttgatttta ctcatccatg tgaccatgag gaatgagag    720 aaatgcttac acacagaaat ggccttgtga aaagggtaa agaacaaaac acacagcgaa    780
gcttttttct cagaatgaag tgtaccctaa ctagccgagg aagaactatg aacataaagt    840
ctgcaacatg gaaggtattg cactgcacag ccacattca cgtatatgat accaacagta    900
accaacctca gtgtgggtat aagaaaccac ctatgacctg cttggtgctg atttgtgaac    960
ccattcctca cccatcaaat attgaaattc ctttagatag caagactttc ctcagtcgac   1020
acagcctgga tatgaaattt tcttattgtg atgaaagaat taccgaattg atgggatatg   1080
agccagaaga acttttaggc cgctcaattt atgaatatta tcatgctttg gactctgatc   1140
atctgaccaa aactcatcat gatatgttta ctaaaggaca agtcaccaca ggacagtaca   1200
ggatgcttgc caaaagaggt ggatatgtct gggttgaaac tcaagcaact gtcatatata   1260
acaccaagaa ttctcaacca cagtgcattg tatgtgtgaa ttacgttgtg agtggtatta   1320
ttcagcacga cttgattttc tcccttcaac aaacagaatg tgtccttaaa ccggttgaat   1380
cttcagatat gaaaatgact cagctattca ccaaagttga atcagaagat acaagtagcc   1440 tcttttgacaa acttaagaag gaacctgatg ctttaacttt gctggcccca gccgctggag   1500
acacaatcat atctttagat tttggcagca acgacacaga aactgatgac cagcaacttg   1560
aggaagtacc attatataat gatgtaatgc tcccctcacc caacgaaaaa ttacagaata   1620
taaatttggc aatgtctcca ttacccaccg ctgaaacgcc aaagccactt cgaagtagtg   1680
ctgaccctgc actcaatcaa gaagttgcat taaaattaga accaaatcca gagtcactgg   1740
aactttcttt taccatgccc cagattcagg atcagacacc tagtccttcc gatggaagca   1800
ctagacaaag ttcacctgag cctaatagtc ccagtgaata ttgttttttat gtggatagtg   1860 atatggtcaa tgaattcaag ttggaattgg tagaaaaact ttttgctgaa gacacagaag   1920
caaagaaccc attttctact caggacacag atttagactt ggagatgtta gctccctata   1980
tcccaatgga tgatgacttc cagttacgtt ccttcgatca gttgtcacca ttagaaagca   2040
gttccgcaag ccctgaaagc gcaagtcctc aaagcacagt tacagtattc cagcagactc   2100
aaatacaaga acctactgct aatgccacca ctaccactgc caccactgat gaattaaaaa   2160
cagtgacaaa agaccgtatg gaagacatta aaatattgat tgcatctcca tctcctaccc   2220
acatacataa agaaactact agtgccacat catcaccata tagagatact caaagtcgga   2280
cagcctcacc aaacagagca ggaaaaggag tcatagaaca gacagaaaaa tctcatccaa   2340
gaagccctaa cgtgttatct gtcgctttga gtcaaagaac tacagttcct gaggaagaac   2400
taaatccaaa gatactagct ttgcagaatg ctcgagaaa gcgaaaaatg gaacatgatg   2460
gttcactttt tcaagcagta ggaattggaa cattattaca gcagccagac gatcatgcag   2520
ctactacatc actttcttgg aaacgtgtaa aaggatgcaa atctagtgaa cagaatggaa   2580
tggagcaaaa gacaattatt ttaatacccct ctgatttagc atgtagactg ctggggcaat   2640
caatggatga aagtgggatta ccacagctga ccagttatga ttgtgaagtt aatgctccta   2700
tacaaggcag cagaaaccta ctgcagggtg aagaattact cagagctttg gatcaagtta   2760
```

```
actgagcttt tcttaatttt cattcctttt tttggacact ggtggctcac tacctaaagc   2820
agtctattta tattttctac atctaatttt agaagcctgg ctacaatact gcacaaactt   2880
ggttagttca attttgatc cccttctac ttaattaca ttaatgctct ttttagtat       2940 gttcttaat  gctggatcac agacagctca ttttctcagt tttttggtat ttaaaccatt   3000
gcattgcagt agcatcattt taaaaatgc  acctttttat ttatttattt ttggctaggg   3060
agtttatccc ttttcgaat  tatttttaag aagatgccaa tataatttt  gtaagaaggc   3120 agtaaccttt catcatgatc ataggcagtt gaaaatttt  tacacctttt ttttcacatt   3180
ttacataaat aataatgctt tgccagcagt acgtggtagc cacaattgca caatatattt   3240
tcttaaaaaa taccagcagt tactcatgga atatattctg cgtttataaa actagttttt   3300
aagaagaaat ttttttggc  ctatgaaatt gttaaacctg gaacatgaca ttgttaatca   3360
tataataatg attcttaaat gctgtatggt ttattattta aatgggtaaa gccatttaca   3420
taatatagaa agatatgcat atatctagaa ggtatgtggc atttatttgg ataaaattct   3480
caattcagag aaatcatctg atgtttctat agtcactttg ccagctcaaa agaaaacaat   3540
accctatgta gttgtggaag tttatgctaa tattgtgtaa ctgatattaa acctaaatgt   3600
tctgcctacc ctgttggtat aaagatattt tgagcagact gtaaacaaga aaaaaaaaat   3660
catgcattct tagcaaaatt gcctagtatg ttaatttgct caaatacaa  tgtttgatttt  3720 tatgcacttt gtcgctatta acatccttt  tttcatgtag atttcaataa ttgagtaatt   3780
ttagaagcat tattttagga atatatagtt gtcacagtaa atatcttgtt ttttctatgt   3840
acattgtaca aattttcat  tccttttgct ctttgtggtt ggatctaaca ctaactgtat   3900
tgttttgtta catcaaataa acatcttctg tggaccagga aaaaaaaaaa aaaaaaa      3958
```

<210> SEQ ID NO 3
<211> LENGTH: 3812
<212> TYPE: DNA
<213> ORGANISM: Homo sapiens

<400> SEQUENCE: 3

```
gtgctgcctc gtctgagggg acaggaggat caccctcttc gtcgcttcgg ccagtgtgtc     60
gggctgggcc ctgacaagcc acctgaggag aggctcggag ccgggcccgg accccggcga    120
ttgccgcccg cttctctcta gtctcacgag gggtttcccg cctcgcaccc ccacctctgg    180
acttgccttt ccttctcttc tccgcgtgtg gagggagcca gcgcttaggc cggagcgagc    240
ctgggggccg cccgccgtga agacatcgcg gggaccgatt caccatggag ggcgccggcg    300
gcgcgaacga caagaaaaag ataagttctg aacgtcgaaa agaaaagtct cgagatgcag    360
ccagatctcg gcgaagtaaa gaatctgaag tttttttatga gcttgctcat cagttgccac    420
ttccacataa tgtgagttcg catcttgata aggcctctgt gatgaggctt accatcagct    480
atttgcgtgt gaggaaactt ctggatgctg gtgatttgga tattgaagat gacatgaaag    540
cacagatgaa ttgctttttat ttgaaagcct tggatggttt tgttatggtt ctcacagatg    600
atggtgacat gatttacatt tctgataatg tgaacaaata catgggatta actcagtttg    660
aactaactgg acacagtgtg tttgatttta ctcatccatg tgaccatgag gaaatgagag    720
aaatgcttac acacagaaat ggccttgtga aaaagggtaa agaacaaaac acacagcgaa    780
gcttttttct cagaatgaag tgtaccctaa ctagccgagg aagaactatg aacataaagt    840
ctgcaacatg gaaggtattg cactgcacag gccacattca cgtatatgat accaacagta    900
accaacctca gtgtgggtat aagaaaccac ctatgacctg cttggtgctg atttgtgaac    960
```

```
ccattcctca cccatcaaat attgaaattc ctttagatag caagactttc ctcagtcgac    1020
acagcctgga tatgaaattt tcttattgtg atgaaagaat taccgaattg atgggatatg    1080
agccagaaga acttttaggc cgctcaattt atgaatatta tcatgctttg gactctgatc    1140
atctgaccaa aactcatcat gatatgttta ctaaaggaca agtcaccaca ggacagtaca    1200
ggatgcttgc caaagaggt ggatatgtct gggttgaaac tcaagcaact gtcatatata    1260
acaccaagaa ttctcaacca cagtgcattg tatgtgtgaa ttacgttgtg agtggtatta    1320
ttcagcacga cttgattttc tcccttcaac aaacagaatg tgtccttaaa ccggttgaat    1380
cttcagatat gaaaatgact cagctattca ccaaagttga atcagaagat acaagtagcc    1440
tctttgacaa acttaagaag gaacctgatg ctttaacttt gctggcccca gccgctggag    1500
acacaatcat atctttagat tttggcagca acgacacaga aactgatgac cagcaacttg    1560
aggaagtacc attatataat gatgtaatgc tcccctcacc caacgaaaaa ttacagaata    1620
taaatttggc aatgtctcca ttacccaccg ctgaaacgcc aaagccactt cgaagtagtg    1680
ctgaccctgc actcaatcaa gaagttgcat taaaattaga accaaatcca gagtcactgg    1740
aactttcttt taccatgccc cagattcagg atcagacacc tagtccttcc gatggaagca    1800
ctagacaaag ttcacctgag cctaatagtc ccagtgaata ttgttttat gtggatagtg    1860 atatggtcaa tgaattcaag ttggaattgg tagaaaaact ttttgctgaa gacacagaag    1920
caaagaaccc attttctact caggacacag atttagactt ggagatgtta gctccctata    1980
tcccaatgga tgatgacttc cagttacgtt ccttcgatca gttgtcacca ttagaaagca    2040
gttccgcaag ccctgaaagc gcaagtcctc aaagcacagt tacagtattc cagcagactc    2100
aaatacaaga acctactgct aatgccacca ctaccactgc caccactgat gaattaaaaa    2160
cagtgacaaa agaccgtatg gaagacatta aaatattgat tgcatctcca tctcctaccc    2220
acatacataa agaaactact agtgccacat catcaccata tagagatact caaagtcgga    2280
cagcctcacc aaacagagca ggaaaaggag tcatagaaca gacagaaaaa tctcatccaa    2340
gaagccctaa cgtgttatct gtcgctttga gtcaaagaac tacagttcct gaggaagaac    2400
taaatccaaa gatactagct ttgcagaatg ctcagagaaa gcgaaaaatg gaacatgatg    2460
gttcactttt tcaagcagta ggaattattt agcatgtaga ctgctggggc aatcaatgga    2520
tgaaagtgga ttaccacagc tgaccagtta tgattgtgaa gttaatgctc ctatacaagg    2580
cagcagaaac ctactgcagg gtgaagaatt actcagagct ttggatcaag ttaactgagc    2640
ttttttctta atttcattcct tttttggac actggtggct cactacctaa agcagtctat    2700
ttatattttc tacatctaat tttagaagcc tggctacaat actgcacaaa cttggttagt    2760 tcaattttg atccccttc tacttaattt acattaatgc tcttttttag tatgttcttt    2820
aatgctggat cacagacagc tcattttctc agttttttgg tatttaaacc attgcattgc    2880
agtagcatca ttttaaaaaa tgcaccttt tatttattta tttttggcta gggagtttat    2940
ccctttttcg aattattttt aagaagatgc caatataatt tttgtaagaa ggcagtaacc    3000
tttcatcatg atcataggca gttgaaaaat ttttacacct tttttttcac attttacata    3060
aataataatg ctttgccagc agtacgtggt agccacaatt gcacaatata ttttcttaaa    3120
aaataccagc agttactcat ggaatatatt ctgcgtttat aaaactagtt tttaagaaga    3180 aattttttt ggcctatgaa attgttaaac ctggaacatg acattgttaa tcatataata    3240
atgattctta aatgctgtat ggtttattat ttaaatgggt aaagccattt acataatata    3300
```

-continued

| | |
|---|---|
| gaaagatatg catatatcta gaaggtatgt ggcatttatt tggataaaat tctcaattca | 3360 |
| gagaaatcat ctgatgtttc tatagtcact ttgccagctc aaaagaaaac aatacccctat | 3420 |
| gtagttgtgg aagtttatgc taatattgtg taactgatat taaacctaaa tgttctgcct | 3480 |
| accctgttgg tataaagata ttttgagcag actgtaaaca agaaaaaaaa aatcatgcat | 3540 |
| tcttagcaaa attgcctagt atgttaattt gctcaaaata caatgtttga tttatgcac | 3600 |
| tttgtcgcta ttaacatcct ttttttcatg tagatttcaa taattgagta attttagaag | 3660 |
| cattattta ggaatatata gttgtcacag taaatatctt gttttttcta tgtacattgt | 3720 |
| acaaattttt cattccttt gctctttgtg gttggatcta cactaactg tattgttttg | 3780 |
| ttacatcaaa taaacatctt ctgtggacca gg | 3812 |

<210> SEQ ID NO 4
<211> LENGTH: 3718
<212> TYPE: DNA
<213> ORGANISM: Rattus norvegicus

<400> SEQUENCE: 4

| | |
|---|---|
| gacaccgcgg gcaccgattc gccatggagg gcgccggcgg cgagaacgag aagaaaaata | 60 |
| ggatgagttc cgaacgtcga aaagaaaagt ctagggatgc agcacgatct cggcgaagca | 120 |
| aagagtctga agtttttat gagcttgctc atcagttgcc acttccccac aacgtgagct | 180 |
| cccatcttga taaagcttct gttatgaggc tcaccatcag ttacttacgt gtgaggaaac | 240 |
| ttctaggtgc tggtgatctt gacattgaag atgaaatgaa agcacagatg aactgctttt | 300 |
| atctgaaagc cctggatggc tttgttatgg tgctaacaga tgatggtgac atgatttaca | 360 |
| tttctgataa cgtgaacaaa tacatggggt tgactcagtt tgaactaact ggacacagtg | 420 |
| tgtttgattt tacccatcca tgtgaccatg aggaaatgag agaaatgctt acacacagaa | 480 |
| atggcccagt gagaaagggg aaagaacaaa acacgcagcg aagcttttt ctcagaatga | 540 |
| aatgtaccct aacaagccgg gggaggacga tgaacatcaa gtcagcaacg tggaaggtgc | 600 |
| tgcactgcac aggccacatt catgtgtatg ataccagcag taaccagccg cagtgtggct | 660 |
| acaagaaacc gcctatgacg tgcttggtgc tgatttgtga acccattcct catccatcaa | 720 |
| acattgaaat tcctttagac agcaagacat ttctcagtcg acacagcctc gatatgaaat | 780 |
| tttcttactg tgatgaaagg attactgagt tgatgggtta tgagccagaa gaacttttgg | 840 |
| gccgttcaat ttatgaatat tatcatgctt tggactctga tcatctgacc aaaactcatc | 900 |
| atgacatgtt tactaaagga caagtcacca caggacagta caggatgctt gcaaaaagag | 960 |
| gtggatatgt ctgggttgag actcaagcaa ctgttatata taatacgaag aactctcagc | 1020 |
| cacagtgcat tgtgtgtgtg aattatgttg taagtggtat tattcagcac gacttgattt | 1080 |
| tctcccttca acaaacagaa tctgtcctca accagttga atcttcagat atgaaaatga | 1140 |
| cccagctgtt cactaaagtg gaatctgagg acacagctg cctcttcgac aagcttaaga | 1200 |
| aagagcccga tgccctgact ctgctagctc cagcggctgg ggacacgatc atatcactgg | 1260 |
| acttcggcag cgatgacacg gaaactgaag accaacaact tgaagatgtc ccgttgtaca | 1320 |
| atgatgtaat gttcccctct tctaatgaga attaaatat aaatctggca atgtctccat | 1380 |
| tacctgcctc tgaaactcca aagccacttc gaagtagtgc tgatcctgca ctgaatcaag | 1440 |
| aggttgcatt gaagttagag tcaagcccag agtcactggg actttctttt accatgcccc | 1500 |
| agattcaaga tcagccagca agtccttctg atggaagcac tagacaaagc tcacctgagc | 1560 |
| ctaacagtcc cagtgagtac tgctttgatg tggacagcga tatggtcaat gtattcaagt | 1620 |

| | |
|---|---|
| tggaactggt ggaaaaactg tttgctgaag acacagaagc gaagaatcca ttttcagctc | 1680 |
| aggacactga tttagacttg gaaatgctgg ctccctatat cccaatggat gatgatttcc | 1740 |
| agttacgttc ctttgatcag ttgtcaccat tagagagcaa ttctccaagc cctccgagtg | 1800 |
| tgagcacagt tacaggattc cagcagaccc agttacagaa acctaccatc actgtcactg | 1860 |
| ccaccgcaac tgccaccact gatgaatcaa aagcagtgac gaaggacaat atagaagaca | 1920 |
| ttaaaatact gattgcatct ccaccttcta cccaagtacc tcaagaaatg accactgcta | 1980 |
| aggcatcagc atacagtggt actcacagtc ggacagcctc accagacaga gcaggaaaga | 2040 |
| gagtcataga aaaaacagac aaagctcatc caaggagcct taacctatct gtcactttga | 2100 |
| atcaaagaaa tactgttcct gaagaagaat taaacccaaa gacaatagct ttgcagaatg | 2160 |
| ctcagaggaa gcgaaaaatg aacatgatg gctcccttttt tcaagcagca ggaattggaa | 2220 |
| cgttactgca gcaaccaggt gaccgtgccc ctactatgtc gctttcttgg aaacgagtga | 2280 |
| aaggatacat atctagtgaa caggatggaa tggagcagaa gacaattttt ttaatacccct | 2340 |
| ctgatttagc atgtagactg ctggggcagt caatggatga gagtggatta ccacagctga | 2400 |
| ccagttacga ttgtgaagtt aatgctccca tacaaggcag cagaaaccta ctgcagggtg | 2460 |
| aagaattact cagagctttg gatcaagtta actgagcttt tcctaatctc attcctttga | 2520 |
| ttgttaattt ttgtgttcag ttgttgttgt tgtctgtggg gtttcgtttc tgttggttgt | 2580 |
| tttggacact ggtggctcag cagtctattt atattttcta tatctcattt agaggcctgg | 2640 |
| ctacagtact gcaccaactc agatagttta gtttgggccc cttcctcctt cattttcact | 2700 |
| gatgctcttt ttaccatgtc cttcgaatgc cagatcacag cacattcaca gctccccagc | 2760 |
| atttcaccaa tgcattgctg tagtgtcgtt taaaatgcac ctttttattt atttattttt | 2820 |
| ggtgagggag tttgtccctt attgaattat ttttaatgaa atgccaatat aattttttaa | 2880 |
| gaaggcagta aatcttcatc atgatgatag gcagttgaaa attttttact catttttttc | 2940 |
| atgttttaca tgaaaataat gctttgccag cagtacatgg tagccacaat tgcacaatat | 3000 |
| attttcttaa aaataccagc agttactcat gcatatattc tgcatttata aaactagttt | 3060 |
| ttaagaagaa acttttttttg gcctatggaa ttgttaagcc tggatcatga tgctgttgat | 3120 |
| cttataatga ttccttaaact gtatggtttc tttatatggg taaagccatt tacatgatat | 3180 |
| agagagatat gcttatatct ggaaggtata tggcatttat ttggataaaa ttctcaattg | 3240 |
| agaagttatc tggtgtttct ttactttacc ggctcaaaag aaaacagtcc ctatgtagtt | 3300 |
| gtggaagctt atgctaatat tgtgtaattg atattaaaca ttaaatgttc tgcctatcct | 3360 |
| gttggtataa agacattttg agcatactgt aaacaaaaaa atcatgcatt gttagtaaaa | 3420 |
| ttgcctagta tgttaatttg ttgaaaatac gatgtttggt tttatgcact ttgtcgctat | 3480 |
| taacatcctt ttttttcatat agatttcaat aattgagtaa ttttagaagc attatttttag | 3540 |
| aaatatagag ttgtcatagt aaacatcttg ttttttttttc tttttttcta tgtacattgt | 3600 |
| ataaattttt cattcccttg ctctttgtag ttgggtctaa cactaactgt actgttttgt | 3660 |
| tatatcaaat aaacatcttc tgtggaccag gaaaaaaaaa aaaaaaaaa aaaaaaaa | 3718 |

<210> SEQ ID NO 5
<211> LENGTH: 3973
<212> TYPE: DNA
<213> ORGANISM: Mus musculus

<400> SEQUENCE: 5

-continued

```
cgcgaggact gtcctcgccg ccgtcgcggg cagtgtctag ccaggccttg acaagctagc      60
cggaggagcg cctaggaacc cgagccgag  ctcagcgagc gcagcctgca cgcccgcctc     120
gcgtcccggg ggggtcccgc ctcccacccc gcctctggac ttgtctcttt ccccgcgcgc     180
gcggacagag ccggcgttta ggcccgagcg agcccggggg ccgccggccg ggaagacaac     240
gcgggcaccg attcgccatg gagggcgccg gcggcgagaa cgagaagaaa aagatgagtt     300
ctgaacgtcg aaaagaaaag tctagagatg cagcaagatc tcggcgaagc aaagagtctg     360 aagttttta  tgagcttgct catcagttgc cacttcccca caatgtgagc tcacatcttg     420
ataaagcttc tgttatgagg ctcaccatca gttatttacg tgtgagaaaa cttctggatg     480
ccggtggtct agacagtgaa gatgagatga aggcacagat ggactgtttt tatctgaaag     540
ccctagatgg ctttgtgatg gtgctaacag atgacggcga catggtttac atttctgata     600
acgtgaacaa atacatgggg ttaactcagt ttgaactaac tggacacagt gtgtttgatt     660
ttactcatcc atgtgaccat gaggaaatga gagaaatgct tacacacaga aatggcccag     720
tgagaaaagg gaaagaacta acacacagc  ggagcttttt tctcagaatg aagtgcaccc     780
taacaagccg ggggaggacg atgaacatca agtcagcaac gtggaaggtg cttcactgca     840
cgggccatat tcatgtctat gataccaaca gtaaccaacc tcagtgtggg tacaagaaac     900
cacccatgac gtgcttggtg ctgatttgtg aacccattcc tcatccgtca atattgaaa      960 ttcctttaga tagcaagaca tttctcagtc gacacagcct cgatatgaaa ttttcttact    1020
gtgatgaaag aattactgag ttgatgggtt atgagccgga agaacttttg ggccgctcaa    1080
tttatgaata ttatcatgct ttggattctg atcatctgac caaaactcac catgatatgt    1140
ttactaaagg acaagtcacc acaggacagt acaggatgct tgccaaaaga ggtggatatg    1200
tctgggttga aactcaagca actgtcatat ataatacgaa gaactcccag ccacagtgca    1260
ttgtgtgtgt gaattatgtt gtaagtggta ttattcagca cgacttgatt ttctcccttc    1320
aacaaacaga atctgtgctc aaaccagttg aatcttcaga tatgaagatg actcagctgt    1380
tcaccaaagt tgaatcagag gatacaagct gccttttga  taagcttaag aaggagcctg    1440
atgctctcac tctgctggct ccagctgccg gcgacaccat catctctctg gattttggca    1500
gcgatgacac agaaactgaa gatcaacaac ttgaagatgt tccattatat aatgatgtaa    1560
tgtttccctc ttctaatgaa aaattaaata taaacctggc aatgtctcct ttaccttcat    1620
cggaaactcc aaagccactt cgaagtagtg ctgatcctgc actgaatcaa gaggttgcat    1680
taaaattaga atcaagtcca gagtcactgg gactttcttt taccatgccc cagattcaag    1740
atcagccagc aagtccttct gatggaagca ctagacaaag ttcacctgag agacttcttc    1800
aggaaaacgt aaacactcct aactttccc  agcctaacag tcccagtgaa tattgctttg    1860
atgtggatag cgatatggtc aatgtattca agttggaact ggtggaaaaa ctgtttgctg    1920
aagcacagag ggcaaagaat ccattttcaa ctcaggacac tgatttagat ttggagatgc    1980
tggctcccta tcccaatg   gatgatgatt ccagttacg  ttcctttgat cagttgtcac    2040
cattagagag caattctcca agccctccaa gtatgagcac agttactggg ttccagcaga    2100
cccagttaca gaaacctacc atcactgcca ctgccaccac aactgccacc actgatgaat    2160
caaaaacaga gacgaaggac aataaagaag atattaaaat actgattgca ctccatcttt    2220
ctacccaagt acctcaagaa acgaccactg ctaaggcatc agcatacagt ggcactcaca    2280
gtcggacagc ctcaccagac agagcaggaa agagagtcat agaacagaca gacaaagctc    2340
atccaaggag ccttaagctg tctgccactt tgaatcaaag aaatactgtt cctgaggaag    2400
```

```
aattaaaccc aagacaata gcttcgcaga atgctcagag gaagcgaaaa atggaacatg    2460
atggctccct ttttcaagca gcaggaattg gaacattatt gcagcaacca ggtgactgtg    2520
cacctactat gtcactttcc tggaaacgag tgaaaggatt catatctagt gaacagaatg    2580
gaacggagca aaagactatt attttaatac cctccgattt agcatgcaga ctgctggggc    2640
agtcaatgga tgagagtgga ttaccacagc tgaccagtta cgattgtgaa gttaatgctc    2700
ccatacaagg cagcagaaac ctactgcagg gtgaagaatt actcagagct ttggatcaag    2760
ttaactgagc gtttcctaat ctcattcctt ttgattgtta atgttttttgt tcagttgttg    2820 ttgtttgttg ggttttttgtt tctgttggtt attttttggac actggtggct cagcagtcta    2880
tttatatttt ctatatctaa ttttagaagc ctggctacaa tactgcacaa actcagatag    2940
tttagttttc atcccctttc tacttaattt tcattaatgc tcttttttaat atgttctttt    3000 aatgccagat cacagcacat tcacagctcc tcagcatttc accattgcat tgctgtagtg    3060
tcatttaaaa tgcaccttttt tatttattta tttttggtga gggagtttgt cccttattga    3120
attattttta atgaaatgcc aatataattt tttaagaaag cagtaaattc tcatcatgat    3180
cataggcagt tgaaaacttt ttactcattt ttttcatgtt ttacatgaaa ataatgcttt    3240
gtcagcagta catggtagcc acaattgcac aatatatttt cttaaaaaa ccagcagtta    3300 ctcatgcaat atattctgca tttataaaac tagttttttaa gaaattttt ttggcctatg    3360 gaattgttaa gcctggatca tgaagcgttg atcttataat gattcttaaa ctgtatggtt    3420
tctttatatg ggtaaagcca tttacatgat ataagaaat atgcttatat ctggaaggta    3480
tgtggcattt atttggataa aattctcaat tcagagaagt tatctggtgt ttcttgactt    3540
taccaactca aaacagtccc tctgtagttg tggaagctta tgctaatatt gtgtaattga    3600
ttatgaaaca taaatgttct gcccaccctg ttggtataaa gacattttga gcatactgta    3660
aacaaacaaa caaaaaatca tgctttgtta gtaaaattgc ctagtatgtt gatttgttga    3720
aaatatgatg tttggttttta tgcactttgt cgctattaac atcctttttt catatagatt    3780
tcaataagtg agtaattttta gaagcattat tttaggaata tagagttgtc atagtaaaca    3840
tcttgttttt tctatgtaca ctgtataaat ttttcgttcc cttgctcttt gtggttgggt    3900
ctaacactaa ctgtactgtt ttgttatatc aaataaacat cttctgtgga ccaggaaaaa    3960 aaaaaaaaa aaa                                                       3973

<210> SEQ ID NO 6
<211> LENGTH: 21
<212> TYPE: DNA
<213> ORGANISM: Artificial Sequence
<220> FEATURE:
<223> OTHER INFORMATION: target sequence

<400> SEQUENCE: 6
aactggacac agtgtgtttg a                                                21

<210> SEQ ID NO 7
<211> LENGTH: 23
<212> TYPE: RNA
<213> ORGANISM: Artificial Sequence
<220> FEATURE:
<223> OTHER INFORMATION: siRNA sense strand

<400> SEQUENCE: 7
aacuaacugg acacagugug uuu                                              23
```

-continued

```
<210> SEQ ID NO 8
<211> LENGTH: 23
<212> TYPE: RNA
<213> ORGANISM: Artificial Sequence
<220> FEATURE:
<223> OTHER INFORMATION: siRNA antisense strand

<400> SEQUENCE: 8
acacacugug uccaguuagu uuu                                              23

<210> SEQ ID NO 9
<211> LENGTH: 23
<212> TYPE: DNA
<213> ORGANISM: Artificial Sequence
<220> FEATURE:
<223> OTHER INFORMATION: siRNA sense strand

<400> SEQUENCE: 9
aacuaacugg acacagugug utt                                              23

<210> SEQ ID NO 10
<211> LENGTH: 23
<212> TYPE: DNA
<213> ORGANISM: Artificial Sequence
<220> FEATURE:
<223> OTHER INFORMATION: siRNA antisense strand

<400> SEQUENCE: 10
acacacugug uccaguuagu utt                                              23

<210> SEQ ID NO 11
<211> LENGTH: 21
<212> TYPE: DNA
<213> ORGANISM: Artificial Sequence
<220> FEATURE:
<223> OTHER INFORMATION: target sequence

<400> SEQUENCE: 11
aactaactgg acacagtgtg t                                                21

<210> SEQ ID NO 12
<211> LENGTH: 17
<212> TYPE: DNA
<213> ORGANISM: Artificial Sequence
<220> FEATURE:
<223> OTHER INFORMATION: target sequence

<400> SEQUENCE: 12
cgacaagaaa aagataa                                                     17

<210> SEQ ID NO 13
<211> LENGTH: 17
<212> TYPE: DNA
<213> ORGANISM: Artificial Sequence
<220> FEATURE:
<223> OTHER INFORMATION: target sequence

<400> SEQUENCE: 13
aaagataagt tctgaac                                                     17

<210> SEQ ID NO 14
<211> LENGTH: 17
<212> TYPE: DNA
<213> ORGANISM: Artificial Sequence
<220> FEATURE:
<223> OTHER INFORMATION: target sequence
```

```
<400> SEQUENCE: 14
agataagttc tgaacgt                                                17

<210> SEQ ID NO 15
<211> LENGTH: 17
<212> TYPE: DNA
<213> ORGANISM: Artificial Sequence
<220> FEATURE:
<223> OTHER INFORMATION: target sequence

<400> SEQUENCE: 15
gttctgaacg tcgaaaa                                                17

<210> SEQ ID NO 16
<211> LENGTH: 17
<212> TYPE: DNA
<213> ORGANISM: Artificial Sequence
<220> FEATURE:
<223> OTHER INFORMATION: target sequence

<400> SEQUENCE: 16
aagaaaagtc tcgagat                                                17

<210> SEQ ID NO 17
<211> LENGTH: 17
<212> TYPE: DNA
<213> ORGANISM: Artificial Sequence
<220> FEATURE:
<223> OTHER INFORMATION: target sequence

<400> SEQUENCE: 17
gaaaagtctc gagatgc                                                17

<210> SEQ ID NO 18
<211> LENGTH: 17
<212> TYPE: DNA
<213> ORGANISM: Artificial Sequence
<220> FEATURE:
<223> OTHER INFORMATION: target sequence

<400> SEQUENCE: 18
agtctcgaga tgcagcc                                                17

<210> SEQ ID NO 19
<211> LENGTH: 17
<212> TYPE: DNA
<213> ORGANISM: Artificial Sequence
<220> FEATURE:
<223> OTHER INFORMATION: target sequence

<400> SEQUENCE: 19
gtaaagaatc tgaagtt                                                17

<210> SEQ ID NO 20
<211> LENGTH: 17
<212> TYPE: DNA
<213> ORGANISM: Artificial Sequence
<220> FEATURE:
<223> OTHER INFORMATION: target sequence

<400> SEQUENCE: 20
gaatctgaag tttttta                                                17

<210> SEQ ID NO 21
```

<211> LENGTH: 17
<212> TYPE: DNA
<213> ORGANISM: Artificial Sequence
<220> FEATURE:
<223> OTHER INFORMATION: target sequence

<400> SEQUENCE: 21
gttttttatg agcttgc                                                    17

<210> SEQ ID NO 22
<211> LENGTH: 17
<212> TYPE: DNA
<213> ORGANISM: Artificial Sequence
<220> FEATURE:
<223> OTHER INFORMATION: target sequence

<400> SEQUENCE: 22
ggcctctgtg atgaggc                                                    17

<210> SEQ ID NO 23
<211> LENGTH: 17
<212> TYPE: DNA
<213> ORGANISM: Artificial Sequence
<220> FEATURE:
<223> OTHER INFORMATION: target sequence

<400> SEQUENCE: 23
cttctggatg ctggtga                                                    17

<210> SEQ ID NO 24
<211> LENGTH: 17
<212> TYPE: DNA
<213> ORGANISM: Artificial Sequence
<220> FEATURE:
<223> OTHER INFORMATION: target sequence

<400> SEQUENCE: 24
agcacagatg aattgct                                                    17

<210> SEQ ID NO 25
<211> LENGTH: 21
<212> TYPE: DNA
<213> ORGANISM: Artificial Sequence
<220> FEATURE:
<223> OTHER INFORMATION: target sequence

<400> SEQUENCE: 25
aaatgcttac acacagaaat g                                               21

<210> SEQ ID NO 26
<211> LENGTH: 17
<212> TYPE: DNA
<213> ORGANISM: Artificial Sequence
<220> FEATURE:
<223> OTHER INFORMATION: target sequence

<400> SEQUENCE: 26
gaaaaagata agttctg                                                    17

<210> SEQ ID NO 27
<211> LENGTH: 17
<212> TYPE: DNA
<213> ORGANISM: Artificial Sequence
<220> FEATURE:
<223> OTHER INFORMATION: target sequence

<400> SEQUENCE: 27

```
aagataagtt ctgaacg                                                      17

<210> SEQ ID NO 28
<211> LENGTH: 17
<212> TYPE: DNA
<213> ORGANISM: Artificial Sequence
<220> FEATURE:
<223> OTHER INFORMATION: target sequence

<400> SEQUENCE: 28
gataagttct gaacgtc                                                      17

<210> SEQ ID NO 29
<211> LENGTH: 17
<212> TYPE: DNA
<213> ORGANISM: Artificial Sequence
<220> FEATURE:
<223> OTHER INFORMATION: target sequence

<400> SEQUENCE: 29
cgtcgaaaag aaaagtc                                                      17

<210> SEQ ID NO 30
<211> LENGTH: 17
<212> TYPE: DNA
<213> ORGANISM: Artificial Sequence
<220> FEATURE:
<223> OTHER INFORMATION: target sequence

<400> SEQUENCE: 30
agaaaagtct cgagatg                                                      17

<210> SEQ ID NO 31
<211> LENGTH: 17
<212> TYPE: DNA
<213> ORGANISM: Artificial Sequence
<220> FEATURE:
<223> OTHER INFORMATION: target sequence

<400> SEQUENCE: 31
aagtctcgag atgcagc                                                      17

<210> SEQ ID NO 32
<211> LENGTH: 17
<212> TYPE: DNA
<213> ORGANISM: Artificial Sequence
<220> FEATURE:
<223> OTHER INFORMATION: target sequence

<400> SEQUENCE: 32
gtctcgagat gcagcca                                                      17

<210> SEQ ID NO 33
<211> LENGTH: 17
<212> TYPE: DNA
<213> ORGANISM: Artificial Sequence
<220> FEATURE:
<223> OTHER INFORMATION: target sequence

<400> SEQUENCE: 33
agaatctgaa gtttttt                                                      17

<210> SEQ ID NO 34
<211> LENGTH: 17
<212> TYPE: DNA
```

```
<213> ORGANISM: Artificial Sequence
<220> FEATURE:
<223> OTHER INFORMATION: target sequence

<400> SEQUENCE: 34
tctgaagttt tttatga                                                    17

<210> SEQ ID NO 35
<211> LENGTH: 17
<212> TYPE: DNA
<213> ORGANISM: Artificial Sequence
<220> FEATURE:
<223> OTHER INFORMATION: target sequence

<400> SEQUENCE: 35
tgtgagttcg catcttg                                                    17

<210> SEQ ID NO 36
<211> LENGTH: 17
<212> TYPE: DNA
<213> ORGANISM: Artificial Sequence
<220> FEATURE:
<223> OTHER INFORMATION: target sequence

<400> SEQUENCE: 36
acttctggat gctggtg                                                    17

<210> SEQ ID NO 37
<211> LENGTH: 17
<212> TYPE: DNA
<213> ORGANISM: Artificial Sequence
<220> FEATURE:
<223> OTHER INFORMATION: target sequence

<400> SEQUENCE: 37
gatgacatga aagcaca                                                    17

<210> SEQ ID NO 38
<211> LENGTH: 17
<212> TYPE: DNA
<213> ORGANISM: Artificial Sequence
<220> FEATURE:
<223> OTHER INFORMATION: target sequence

<400> SEQUENCE: 38
gcacagatga attgctt                                                    17

<210> SEQ ID NO 39
<211> LENGTH: 21
<212> TYPE: DNA
<213> ORGANISM: Artificial Sequence
<220> FEATURE:
<223> OTHER INFORMATION: target sequence

<400> SEQUENCE: 39 aagttttta tgagcttgct c                                                21

<210> SEQ ID NO 40
<211> LENGTH: 21
<212> TYPE: DNA
<213> ORGANISM: Artificial Sequence
<220> FEATURE:
<223> OTHER INFORMATION: target sequence

<400> SEQUENCE: 40 aagttttta tgagcttgct c                                                21
```

-continued

<210> SEQ ID NO 41
<211> LENGTH: 21
<212> TYPE: DNA
<213> ORGANISM: Artificial Sequence
<220> FEATURE:
<223> OTHER INFORMATION: target sequence

<400> SEQUENCE: 41
aaggcctctg tgatgaggct t                                              21

<210> SEQ ID NO 42
<211> LENGTH: 21
<212> TYPE: DNA
<213> ORGANISM: Artificial Sequence
<220> FEATURE:
<223> OTHER INFORMATION: target sequence

<400> SEQUENCE: 42
aaacttctgg atgctggtga t                                              21

<210> SEQ ID NO 43
<211> LENGTH: 21
<212> TYPE: DNA
<213> ORGANISM: Artificial Sequence
<220> FEATURE:
<223> OTHER INFORMATION: target sequence

<400> SEQUENCE: 43
aacttctgga tgctggtgat t                                              21

<210> SEQ ID NO 44
<211> LENGTH: 21
<212> TYPE: DNA
<213> ORGANISM: Artificial Sequence
<220> FEATURE:
<223> OTHER INFORMATION: target sequence

<400> SEQUENCE: 44
aagatgacat gaaagcacag a                                              21

<210> SEQ ID NO 45
<211> LENGTH: 21
<212> TYPE: DNA
<213> ORGANISM: Artificial Sequence
<220> FEATURE:
<223> OTHER INFORMATION: target sequence

<400> SEQUENCE: 45
aaagcacaga tgaattgctt t                                              21

<210> SEQ ID NO 46
<211> LENGTH: 21
<212> TYPE: DNA
<213> ORGANISM: Artificial Sequence
<220> FEATURE:
<223> OTHER INFORMATION: target sequence

<400> SEQUENCE: 46
aagcacagat gaattgcttt t                                              21

<210> SEQ ID NO 47
<211> LENGTH: 21
<212> TYPE: DNA
<213> ORGANISM: Artificial Sequence
<220> FEATURE:

```
<223> OTHER INFORMATION: target sequence

<400> SEQUENCE: 47
aattgctttt atttgaaagc c                                              21

<210> SEQ ID NO 48
<211> LENGTH: 21
<212> TYPE: DNA
<213> ORGANISM: Artificial Sequence
<220> FEATURE:
<223> OTHER INFORMATION: target sequence

<400> SEQUENCE: 48
aaagccttgg atggttttgt t                                              21

<210> SEQ ID NO 49
<211> LENGTH: 21
<212> TYPE: DNA
<213> ORGANISM: Artificial Sequence
<220> FEATURE:
<223> OTHER INFORMATION: target sequence

<400> SEQUENCE: 49
aagccttgga tggttttgtt a                                              21

<210> SEQ ID NO 50
<211> LENGTH: 21
<212> TYPE: DNA
<213> ORGANISM: Artificial Sequence
<220> FEATURE:
<223> OTHER INFORMATION: target sequence

<400> SEQUENCE: 50
aatgtgaaca aatacatggg a                                              21

<210> SEQ ID NO 51
<211> LENGTH: 21
<212> TYPE: DNA
<213> ORGANISM: Artificial Sequence
<220> FEATURE:
<223> OTHER INFORMATION: target sequence

<400> SEQUENCE: 51
aacaaataca tgggattaac t                                              21

<210> SEQ ID NO 52
<211> LENGTH: 21
<212> TYPE: DNA
<213> ORGANISM: Artificial Sequence
<220> FEATURE:
<223> OTHER INFORMATION: target sequence

<400> SEQUENCE: 52
aaatacatgg gattaactca g                                              21

<210> SEQ ID NO 53
<211> LENGTH: 21
<212> TYPE: DNA
<213> ORGANISM: Artificial Sequence
<220> FEATURE:
<223> OTHER INFORMATION: target sequence

<400> SEQUENCE: 53
aaatacatgg gattaactca g                                              21
```

```
<210> SEQ ID NO 54
<211> LENGTH: 21
<212> TYPE: DNA
<213> ORGANISM: Artificial Sequence
<220> FEATURE:
<223> OTHER INFORMATION: target sequence

<400> SEQUENCE: 54
aactcagttt gaactaactg g                                              21

<210> SEQ ID NO 55
<211> LENGTH: 21
<212> TYPE: DNA
<213> ORGANISM: Artificial Sequence
<220> FEATURE:
<223> OTHER INFORMATION: target sequence

<400> SEQUENCE: 55
aactaactgg acacagtgtg t                                              21

<210> SEQ ID NO 56
<211> LENGTH: 21
<212> TYPE: DNA
<213> ORGANISM: Artificial Sequence
<220> FEATURE:
<223> OTHER INFORMATION: target sequence

<400> SEQUENCE: 56
aactggacac agtgtgtttg a                                              21

<210> SEQ ID NO 57
<211> LENGTH: 21
<212> TYPE: DNA
<213> ORGANISM: Artificial Sequence
<220> FEATURE:
<223> OTHER INFORMATION: target sequence

<400> SEQUENCE: 57
aaatgagaga aatgcttaca c                                              21

<210> SEQ ID NO 58
<211> LENGTH: 21
<212> TYPE: DNA
<213> ORGANISM: Artificial Sequence
<220> FEATURE:
<223> OTHER INFORMATION: target sequence

<400> SEQUENCE: 58
aatgagagaa atgcttacac a                                              21

<210> SEQ ID NO 59
<211> LENGTH: 21
<212> TYPE: DNA
<213> ORGANISM: Artificial Sequence
<220> FEATURE:
<223> OTHER INFORMATION: target sequence

<400> SEQUENCE: 59
aaatgcttac acacagaaat g                                              21

<210> SEQ ID NO 60
<211> LENGTH: 21
<212> TYPE: DNA
<213> ORGANISM: Artificial Sequence
<220> FEATURE:
<223> OTHER INFORMATION: target sequence
```

```
<400> SEQUENCE: 60
aatgcttaca cacagaaatg g                                              21

<210> SEQ ID NO 61
<211> LENGTH: 21
<212> TYPE: DNA
<213> ORGANISM: Artificial Sequence
<220> FEATURE:
<223> OTHER INFORMATION: target sequence

<400> SEQUENCE: 61
aaatggcctt gtgaaaaagg g                                              21

<210> SEQ ID NO 62
<211> LENGTH: 21
<212> TYPE: DNA
<213> ORGANISM: Artificial Sequence
<220> FEATURE:
<223> OTHER INFORMATION: target sequence

<400> SEQUENCE: 62
aatggccttg tgaaaagggt                                                21

<210> SEQ ID NO 63
<211> LENGTH: 21
<212> TYPE: DNA
<213> ORGANISM: Artificial Sequence
<220> FEATURE:
<223> OTHER INFORMATION: target sequence

<400> SEQUENCE: 63
aaaaagggta agaacaaaa c                                               21

<210> SEQ ID NO 64
<211> LENGTH: 21
<212> TYPE: DNA
<213> ORGANISM: Artificial Sequence
<220> FEATURE:
<223> OTHER INFORMATION: target sequence

<400> SEQUENCE: 64
aaaagggtaa agaacaaaac a                                              21

<210> SEQ ID NO 65
<211> LENGTH: 21
<212> TYPE: DNA
<213> ORGANISM: Artificial Sequence
<220> FEATURE:
<223> OTHER INFORMATION: target sequence

<400> SEQUENCE: 65
aaagggtaaa gaacaaaaca c                                              21

<210> SEQ ID NO 66
<211> LENGTH: 21
<212> TYPE: DNA
<213> ORGANISM: Artificial Sequence
<220> FEATURE:
<223> OTHER INFORMATION: target sequence

<400> SEQUENCE: 66
aagggtaaag aacaaaacac a                                              21

<210> SEQ ID NO 67
<211> LENGTH: 21
```

```
<212> TYPE: DNA
<213> ORGANISM: Artificial Sequence
<220> FEATURE:
<223> OTHER INFORMATION: target sequence

<400> SEQUENCE: 67
aaagaacaaa acacacagcg a                                              21

<210> SEQ ID NO 68
<211> LENGTH: 21
<212> TYPE: DNA
<213> ORGANISM: Artificial Sequence
<220> FEATURE:
<223> OTHER INFORMATION: target sequence

<400> SEQUENCE: 68
aagaacaaaa cacacagcga a                                              21

<210> SEQ ID NO 69
<211> LENGTH: 21
<212> TYPE: DNA
<213> ORGANISM: Artificial Sequence
<220> FEATURE:
<223> OTHER INFORMATION: target sequence

<400> SEQUENCE: 69
aacaaaacac acagcgaagc t                                              21

<210> SEQ ID NO 70
<211> LENGTH: 21
<212> TYPE: DNA
<213> ORGANISM: Artificial Sequence
<220> FEATURE:
<223> OTHER INFORMATION: target sequence

<400> SEQUENCE: 70
aacaaaacac acagcgaagc t                                              21

<210> SEQ ID NO 71
<211> LENGTH: 21
<212> TYPE: DNA
<213> ORGANISM: Artificial Sequence
<220> FEATURE:
<223> OTHER INFORMATION: target sequence

<400> SEQUENCE: 71
aaacacacag cgaagctttt t                                              21

<210> SEQ ID NO 72
<211> LENGTH: 21
<212> TYPE: DNA
<213> ORGANISM: Artificial Sequence
<220> FEATURE:
<223> OTHER INFORMATION: target sequence

<400> SEQUENCE: 72
aacacacagc gaagcttttt t                                              21

<210> SEQ ID NO 73
<211> LENGTH: 21
<212> TYPE: DNA
<213> ORGANISM: Artificial Sequence
<220> FEATURE:
<223> OTHER INFORMATION: target sequence

<400> SEQUENCE: 73
```

-continued

```
aagctttttt ctcagaatga a                                              21
```

<210> SEQ ID NO 74
<211> LENGTH: 21
<212> TYPE: DNA
<213> ORGANISM: Artificial Sequence
<220> FEATURE:
<223> OTHER INFORMATION: target sequence

<400> SEQUENCE: 74

```
aatgaagtgt accctaacta g                                              21
```

<210> SEQ ID NO 75
<211> LENGTH: 21
<212> TYPE: DNA
<213> ORGANISM: Artificial Sequence
<220> FEATURE:
<223> OTHER INFORMATION: target sequence

<400> SEQUENCE: 75

```
aagtgtaccc taactagccg a                                              21
```

<210> SEQ ID NO 76
<211> LENGTH: 21
<212> TYPE: DNA
<213> ORGANISM: Artificial Sequence
<220> FEATURE:
<223> OTHER INFORMATION: target sequence

<400> SEQUENCE: 76

```
aactagccga ggaagaacta t                                              21
```

<210> SEQ ID NO 77
<211> LENGTH: 21
<212> TYPE: DNA
<213> ORGANISM: Artificial Sequence
<220> FEATURE:
<223> OTHER INFORMATION: target sequence

<400> SEQUENCE: 77

```
aagaactatg aacataaagt c                                              21
```

<210> SEQ ID NO 78
<211> LENGTH: 21
<212> TYPE: DNA
<213> ORGANISM: Artificial Sequence
<220> FEATURE:
<223> OTHER INFORMATION: target sequence

<400> SEQUENCE: 78

```
aactatgaac ataaagtctg c                                              21
```

<210> SEQ ID NO 79
<211> LENGTH: 21
<212> TYPE: DNA
<213> ORGANISM: Artificial Sequence
<220> FEATURE:
<223> OTHER INFORMATION: target sequence

<400> SEQUENCE: 79

```
aacataaagt ctgcaacatg g                                              21
```

<210> SEQ ID NO 80
<211> LENGTH: 21
<212> TYPE: DNA
<213> ORGANISM: Artificial Sequence -continued

```
<220> FEATURE:
<223> OTHER INFORMATION: target sequence

<400> SEQUENCE: 80
aaagtctgca acatggaagg t                                              21

<210> SEQ ID NO 81
<211> LENGTH: 21
<212> TYPE: DNA
<213> ORGANISM: Artificial Sequence
<220> FEATURE:
<223> OTHER INFORMATION: target sequence

<400> SEQUENCE: 81
aagtctgcaa catggaaggt a                                              21

<210> SEQ ID NO 82
<211> LENGTH: 21
<212> TYPE: DNA
<213> ORGANISM: Artificial Sequence
<220> FEATURE:
<223> OTHER INFORMATION: target sequence

<400> SEQUENCE: 82
aacatggaag gtattgcact g                                              21

<210> SEQ ID NO 83
<211> LENGTH: 21
<212> TYPE: DNA
<213> ORGANISM: Artificial Sequence
<220> FEATURE:
<223> OTHER INFORMATION: target sequence

<400> SEQUENCE: 83
aaggtattgc actgcacagg c                                              21

<210> SEQ ID NO 84
<211> LENGTH: 21
<212> TYPE: DNA
<213> ORGANISM: Artificial Sequence
<220> FEATURE:
<223> OTHER INFORMATION: target sequence

<400> SEQUENCE: 84
aacagtaacc aacctcagtg t                                              21

<210> SEQ ID NO 85
<211> LENGTH: 21
<212> TYPE: DNA
<213> ORGANISM: Artificial Sequence
<220> FEATURE:
<223> OTHER INFORMATION: target sequence

<400> SEQUENCE: 85
aaccaacctc agtgtgggta t                                              21

<210> SEQ ID NO 86
<211> LENGTH: 21
<212> TYPE: DNA
<213> ORGANISM: Artificial Sequence
<220> FEATURE:
<223> OTHER INFORMATION: target sequence

<400> SEQUENCE: 86
aacctcagtg tgggtataag a                                              21
```

<210> SEQ ID NO 87
<211> LENGTH: 21
<212> TYPE: DNA
<213> ORGANISM: Artificial Sequence
<220> FEATURE:
<223> OTHER INFORMATION: target sequence

<400> SEQUENCE: 87
aagaaaccac ctatgacctg c                                              21

<210> SEQ ID NO 88
<211> LENGTH: 21
<212> TYPE: DNA
<213> ORGANISM: Artificial Sequence
<220> FEATURE:
<223> OTHER INFORMATION: target sequence

<400> SEQUENCE: 88
aagaaaccac ctatgacctg c                                              21

<210> SEQ ID NO 89
<211> LENGTH: 21
<212> TYPE: DNA
<213> ORGANISM: Artificial Sequence
<220> FEATURE:
<223> OTHER INFORMATION: target sequence

<400> SEQUENCE: 89
aaccacctat gacctgcttg g                                              21

<210> SEQ ID NO 90
<211> LENGTH: 21
<212> TYPE: DNA
<213> ORGANISM: Artificial Sequence
<220> FEATURE:
<223> OTHER INFORMATION: target sequence

<400> SEQUENCE: 90
aacccattcc tcacccatca a                                              21

<210> SEQ ID NO 91
<211> LENGTH: 21
<212> TYPE: DNA
<213> ORGANISM: Artificial Sequence
<220> FEATURE:
<223> OTHER INFORMATION: target sequence

<400> SEQUENCE: 91
aaatattgaa attcctttag a                                              21

<210> SEQ ID NO 92
<211> LENGTH: 21
<212> TYPE: DNA
<213> ORGANISM: Artificial Sequence
<220> FEATURE:
<223> OTHER INFORMATION: target sequence

<400> SEQUENCE: 92
aatattgaaa ttcctttaga t                                              21

<210> SEQ ID NO 93
<211> LENGTH: 21
<212> TYPE: DNA
<213> ORGANISM: Artificial Sequence
<220> FEATURE:
<223> OTHER INFORMATION: target sequence

```
<400> SEQUENCE: 93
aaattccttt agatagcaag a                                              21

<210> SEQ ID NO 94
<211> LENGTH: 21
<212> TYPE: DNA
<213> ORGANISM: Artificial Sequence
<220> FEATURE:
<223> OTHER INFORMATION: target sequence

<400> SEQUENCE: 94
aattccttta gatagcaaga c                                              21

<210> SEQ ID NO 95
<211> LENGTH: 21
<212> TYPE: DNA
<213> ORGANISM: Artificial Sequence
<220> FEATURE:
<223> OTHER INFORMATION: target sequence

<400> SEQUENCE: 95
aagactttcc tcagtcgaca c                                              21

<210> SEQ ID NO 96
<211> LENGTH: 21
<212> TYPE: DNA
<213> ORGANISM: Artificial Sequence
<220> FEATURE:
<223> OTHER INFORMATION: target sequence

<400> SEQUENCE: 96
aaattttctt attgtgatga a                                              21

<210> SEQ ID NO 97
<211> LENGTH: 21
<212> TYPE: DNA
<213> ORGANISM: Artificial Sequence
<220> FEATURE:
<223> OTHER INFORMATION: target sequence

<400> SEQUENCE: 97
aattttctta ttgtgatgaa a                                              21

<210> SEQ ID NO 98
<211> LENGTH: 21
<212> TYPE: DNA
<213> ORGANISM: Artificial Sequence
<220> FEATURE:
<223> OTHER INFORMATION: target sequence

<400> SEQUENCE: 98
aaagaattac cgaattgatg g                                              21

<210> SEQ ID NO 99
<211> LENGTH: 21
<212> TYPE: DNA
<213> ORGANISM: Artificial Sequence
<220> FEATURE:
<223> OTHER INFORMATION: target sequence

<400> SEQUENCE: 99
aattaccgaa ttgatgggat a                                              21

<210> SEQ ID NO 100
```

```
<211> LENGTH: 21
<212> TYPE: DNA
<213> ORGANISM: Artificial Sequence
<220> FEATURE:
<223> OTHER INFORMATION: target sequence

<400> SEQUENCE: 100
aattaccgaa ttgatgggat a                                              21

<210> SEQ ID NO 101
<211> LENGTH: 21
<212> TYPE: DNA
<213> ORGANISM: Artificial Sequence
<220> FEATURE:
<223> OTHER INFORMATION: target sequence

<400> SEQUENCE: 101
aagaactttt aggccgctca a                                              21

<210> SEQ ID NO 102
<211> LENGTH: 21
<212> TYPE: DNA
<213> ORGANISM: Artificial Sequence
<220> FEATURE:
<223> OTHER INFORMATION: target sequence

<400> SEQUENCE: 102
aacttttagg ccgctcaatt t                                              21

<210> SEQ ID NO 103
<211> LENGTH: 21
<212> TYPE: DNA
<213> ORGANISM: Artificial Sequence
<220> FEATURE:
<223> OTHER INFORMATION: target sequence

<400> SEQUENCE: 103
aatttatgaa tattatcatg c                                              21

<210> SEQ ID NO 104
<211> LENGTH: 21
<212> TYPE: DNA
<213> ORGANISM: Artificial Sequence
<220> FEATURE:
<223> OTHER INFORMATION: target sequence

<400> SEQUENCE: 104
aatattatca tgctttggac t                                              21

<210> SEQ ID NO 105
<211> LENGTH: 21
<212> TYPE: DNA
<213> ORGANISM: Artificial Sequence
<220> FEATURE:
<223> OTHER INFORMATION: target sequence

<400> SEQUENCE: 105
aaaactcatc atgatatgtt t                                              21

<210> SEQ ID NO 106
<211> LENGTH: 21
<212> TYPE: DNA
<213> ORGANISM: Artificial Sequence
<220> FEATURE:
<223> OTHER INFORMATION: target sequence

<400> SEQUENCE: 106
```

```
aaactcatca tgatatgttt a                                              21

<210> SEQ ID NO 107
<211> LENGTH: 21
<212> TYPE: DNA
<213> ORGANISM: Artificial Sequence
<220> FEATURE:
<223> OTHER INFORMATION: target sequence

<400> SEQUENCE: 107
aactcatcat gatatgttta c                                              21

<210> SEQ ID NO 108
<211> LENGTH: 21
<212> TYPE: DNA
<213> ORGANISM: Artificial Sequence
<220> FEATURE:
<223> OTHER INFORMATION: target sequence

<400> SEQUENCE: 108
aaaggacaag tcaccacagg a                                              21

<210> SEQ ID NO 109
<211> LENGTH: 21
<212> TYPE: DNA
<213> ORGANISM: Artificial Sequence
<220> FEATURE:
<223> OTHER INFORMATION: target sequence

<400> SEQUENCE: 109
aaggacaagt caccacagga c                                              21

<210> SEQ ID NO 110
<211> LENGTH: 21
<212> TYPE: DNA
<213> ORGANISM: Artificial Sequence
<220> FEATURE:
<223> OTHER INFORMATION: target sequence

<400> SEQUENCE: 110
aagtcaccac aggacagtac a                                              21

<210> SEQ ID NO 111
<211> LENGTH: 21
<212> TYPE: DNA
<213> ORGANISM: Artificial Sequence
<220> FEATURE:
<223> OTHER INFORMATION: target sequence

<400> SEQUENCE: 111
aaaagaggtg gatatgtctg g                                              21

<210> SEQ ID NO 112
<211> LENGTH: 21
<212> TYPE: DNA
<213> ORGANISM: Artificial Sequence
<220> FEATURE:
<223> OTHER INFORMATION: target sequence

<400> SEQUENCE: 112
aaagaggtgg atatgtctgg g                                              21

<210> SEQ ID NO 113
<211> LENGTH: 21
<212> TYPE: DNA
```

```
<213> ORGANISM: Artificial Sequence
<220> FEATURE:
<223> OTHER INFORMATION: target sequence

<400> SEQUENCE: 113
aagaggtgga tatgtctggg t                                              21

<210> SEQ ID NO 114
<211> LENGTH: 21
<212> TYPE: DNA
<213> ORGANISM: Artificial Sequence
<220> FEATURE:
<223> OTHER INFORMATION: target sequence

<400> SEQUENCE: 114
aaactcaagc aactgtcata t                                              21

<210> SEQ ID NO 115
<211> LENGTH: 21
<212> TYPE: DNA
<213> ORGANISM: Artificial Sequence
<220> FEATURE:
<223> OTHER INFORMATION: target sequence

<400> SEQUENCE: 115
aactcaagca actgtcatat a                                              21

<210> SEQ ID NO 116
<211> LENGTH: 21
<212> TYPE: DNA
<213> ORGANISM: Artificial Sequence
<220> FEATURE:
<223> OTHER INFORMATION: target sequence

<400> SEQUENCE: 116
aagcaactgt catatataac a                                              21

<210> SEQ ID NO 117
<211> LENGTH: 21
<212> TYPE: DNA
<213> ORGANISM: Artificial Sequence
<220> FEATURE:
<223> OTHER INFORMATION: target sequence

<400> SEQUENCE: 117
aactgtcata tataacacca a                                              21

<210> SEQ ID NO 118
<211> LENGTH: 21
<212> TYPE: DNA
<213> ORGANISM: Artificial Sequence
<220> FEATURE:
<223> OTHER INFORMATION: target sequence

<400> SEQUENCE: 118
aacaccaaga attctcaacc a                                              21

<210> SEQ ID NO 119
<211> LENGTH: 21
<212> TYPE: DNA
<213> ORGANISM: Artificial Sequence
<220> FEATURE:
<223> OTHER INFORMATION: target sequence

<400> SEQUENCE: 119
aagaattctc aaccacagtg c                                              21
```

<210> SEQ ID NO 120
<211> LENGTH: 21
<212> TYPE: DNA
<213> ORGANISM: Artificial Sequence
<220> FEATURE:
<223> OTHER INFORMATION: target sequence

<400> SEQUENCE: 120
aattctcaac cacagtgcat t                                              21

<210> SEQ ID NO 121
<211> LENGTH: 21
<212> TYPE: DNA
<213> ORGANISM: Artificial Sequence
<220> FEATURE:
<223> OTHER INFORMATION: target sequence

<400> SEQUENCE: 121
aaccacagtg cattgtatgt g                                              21

<210> SEQ ID NO 122
<211> LENGTH: 21
<212> TYPE: DNA
<213> ORGANISM: Artificial Sequence
<220> FEATURE:
<223> OTHER INFORMATION: target sequence

<400> SEQUENCE: 122
aattacgttg tgagtggtat t                                              21

<210> SEQ ID NO 123
<211> LENGTH: 21
<212> TYPE: DNA
<213> ORGANISM: Artificial Sequence
<220> FEATURE:
<223> OTHER INFORMATION: target sequence

<400> SEQUENCE: 123
aacaaacaga atgtgtcctt a                                              21

<210> SEQ ID NO 124
<211> LENGTH: 21
<212> TYPE: DNA
<213> ORGANISM: Artificial Sequence
<220> FEATURE:
<223> OTHER INFORMATION: target sequence

<400> SEQUENCE: 124
aaacagaatg tgtccttaaa c                                              21

<210> SEQ ID NO 125
<211> LENGTH: 21
<212> TYPE: DNA
<213> ORGANISM: Artificial Sequence
<220> FEATURE:
<223> OTHER INFORMATION: target sequence

<400> SEQUENCE: 125
aacagaatgt gtccttaaac c                                              21

<210> SEQ ID NO 126
<211> LENGTH: 20
<212> TYPE: DNA
<213> ORGANISM: Artificial Sequence
<220> FEATURE:

```
<223> OTHER INFORMATION: target sequence

<400> SEQUENCE: 126
atgtgtcctt aaaccggttg                                              20

<210> SEQ ID NO 127
<211> LENGTH: 21
<212> TYPE: DNA
<213> ORGANISM: Artificial Sequence
<220> FEATURE:
<223> OTHER INFORMATION: target sequence

<400> SEQUENCE: 127
aaaccggttg aatcttcaga t                                            21

<210> SEQ ID NO 128
<211> LENGTH: 21
<212> TYPE: DNA
<213> ORGANISM: Artificial Sequence
<220> FEATURE:
<223> OTHER INFORMATION: target sequence

<400> SEQUENCE: 128
aaccggttga atcttcagat a                                            21

<210> SEQ ID NO 129
<211> LENGTH: 21
<212> TYPE: DNA
<213> ORGANISM: Artificial Sequence
<220> FEATURE:
<223> OTHER INFORMATION: target sequence

<400> SEQUENCE: 129
aatcttcaga tatgaaaatg a                                            21

<210> SEQ ID NO 130
<211> LENGTH: 21
<212> TYPE: DNA
<213> ORGANISM: Artificial Sequence
<220> FEATURE:
<223> OTHER INFORMATION: target sequence

<400> SEQUENCE: 130
aaaatgactc agctattcac c                                            21

<210> SEQ ID NO 131
<211> LENGTH: 21
<212> TYPE: DNA
<213> ORGANISM: Artificial Sequence
<220> FEATURE:
<223> OTHER INFORMATION: target sequence

<400> SEQUENCE: 131
aaatgactca gctattcacc a                                            21

<210> SEQ ID NO 132
<211> LENGTH: 21
<212> TYPE: DNA
<213> ORGANISM: Artificial Sequence
<220> FEATURE:
<223> OTHER INFORMATION: target sequence

<400> SEQUENCE: 132
aatgactcag ctattcacca a                                            21
```

<210> SEQ ID NO 133
<211> LENGTH: 21
<212> TYPE: DNA
<213> ORGANISM: Artificial Sequence
<220> FEATURE:
<223> OTHER INFORMATION: target sequence

<400> SEQUENCE: 133
aaagttgaat cagaagatac a                                             21

<210> SEQ ID NO 134
<211> LENGTH: 21
<212> TYPE: DNA
<213> ORGANISM: Artificial Sequence
<220> FEATURE:
<223> OTHER INFORMATION: target sequence

<400> SEQUENCE: 134
aagttgaatc agaagataca a                                             21

<210> SEQ ID NO 135
<211> LENGTH: 21
<212> TYPE: DNA
<213> ORGANISM: Artificial Sequence
<220> FEATURE:
<223> OTHER INFORMATION: target sequence

<400> SEQUENCE: 135
aatcagaaga tacaagtagc c                                             21

<210> SEQ ID NO 136
<211> LENGTH: 21
<212> TYPE: DNA
<213> ORGANISM: Artificial Sequence
<220> FEATURE:
<223> OTHER INFORMATION: target sequence

<400> SEQUENCE: 136
aagatacaag tagcctcttt g                                             21

<210> SEQ ID NO 137
<211> LENGTH: 21
<212> TYPE: DNA
<213> ORGANISM: Artificial Sequence
<220> FEATURE:
<223> OTHER INFORMATION: target sequence

<400> SEQUENCE: 137
aagtagcctc tttgacaaac t                                             21

<210> SEQ ID NO 138
<211> LENGTH: 21
<212> TYPE: DNA
<213> ORGANISM: Artificial Sequence
<220> FEATURE:
<223> OTHER INFORMATION: target sequence

<400> SEQUENCE: 138
aaacttaaga aggaacctga t                                             21

<210> SEQ ID NO 139
<211> LENGTH: 21
<212> TYPE: DNA
<213> ORGANISM: Artificial Sequence
<220> FEATURE:
<223> OTHER INFORMATION: target sequence -continued

```
<400> SEQUENCE: 139
aacttaagaa ggaacctgat g                                              21

<210> SEQ ID NO 140
<211> LENGTH: 21
<212> TYPE: DNA
<213> ORGANISM: Artificial Sequence
<220> FEATURE:
<223> OTHER INFORMATION: target sequence

<400> SEQUENCE: 140
aagaaggaac ctgatgcttt a                                              21

<210> SEQ ID NO 141
<211> LENGTH: 21
<212> TYPE: DNA
<213> ORGANISM: Artificial Sequence
<220> FEATURE:
<223> OTHER INFORMATION: target sequence

<400> SEQUENCE: 141
aaggaacctg atgctttaac t                                              21

<210> SEQ ID NO 142
<211> LENGTH: 21
<212> TYPE: DNA
<213> ORGANISM: Artificial Sequence
<220> FEATURE:
<223> OTHER INFORMATION: target sequence

<400> SEQUENCE: 142
aacctgatgc tttaactttg c                                              21

<210> SEQ ID NO 143
<211> LENGTH: 21
<212> TYPE: DNA
<213> ORGANISM: Artificial Sequence
<220> FEATURE:
<223> OTHER INFORMATION: target sequence

<400> SEQUENCE: 143
aactttgctg gccccagccg c                                              21

<210> SEQ ID NO 144
<211> LENGTH: 21
<212> TYPE: DNA
<213> ORGANISM: Artificial Sequence
<220> FEATURE:
<223> OTHER INFORMATION: target sequence

<400> SEQUENCE: 144
aatcatatct ttagattttg g                                              21

<210> SEQ ID NO 145
<211> LENGTH: 21
<212> TYPE: DNA
<213> ORGANISM: Artificial Sequence
<220> FEATURE:
<223> OTHER INFORMATION: target sequence

<400> SEQUENCE: 145
aacgacacag aaactgatga c                                              21

<210> SEQ ID NO 146
<211> LENGTH: 21
```

```
<212> TYPE: DNA
<213> ORGANISM: Artificial Sequence
<220> FEATURE:
<223> OTHER INFORMATION: target sequence

<400> SEQUENCE: 146
aaactgatga ccagcaactt g                                              21

<210> SEQ ID NO 147
<211> LENGTH: 21
<212> TYPE: DNA
<213> ORGANISM: Artificial Sequence
<220> FEATURE:
<223> OTHER INFORMATION: target sequence

<400> SEQUENCE: 147
aactgatgac cagcaacttg a                                              21

<210> SEQ ID NO 148
<211> LENGTH: 21
<212> TYPE: DNA
<213> ORGANISM: Artificial Sequence
<220> FEATURE:
<223> OTHER INFORMATION: target sequence

<400> SEQUENCE: 148
aacttgagga agtaccatta t                                              21

<210> SEQ ID NO 149
<211> LENGTH: 21
<212> TYPE: DNA
<213> ORGANISM: Artificial Sequence
<220> FEATURE:
<223> OTHER INFORMATION: target sequence

<400> SEQUENCE: 149
aagtaccatt atataatgat g                                              21

<210> SEQ ID NO 150
<211> LENGTH: 21
<212> TYPE: DNA
<213> ORGANISM: Artificial Sequence
<220> FEATURE:
<223> OTHER INFORMATION: target sequence

<400> SEQUENCE: 150
aatgatgtaa tgctcccctc a                                              21

<210> SEQ ID NO 151
<211> LENGTH: 21
<212> TYPE: DNA
<213> ORGANISM: Artificial Sequence
<220> FEATURE:
<223> OTHER INFORMATION: target sequence

<400> SEQUENCE: 151
aatgctcccc tcacccaacg a                                              21

<210> SEQ ID NO 152
<211> LENGTH: 21
<212> TYPE: DNA
<213> ORGANISM: Artificial Sequence
<220> FEATURE:
<223> OTHER INFORMATION: target sequence

<400> SEQUENCE: 152
```
aacgaaaaat tacagaatat a                                              21

<210> SEQ ID NO 153
<211> LENGTH: 21
<212> TYPE: DNA
<213> ORGANISM: Artificial Sequence
<220> FEATURE:
<223> OTHER INFORMATION: target sequence

<400> SEQUENCE: 153
aaaaattaca gaatataaat t                                              21

<210> SEQ ID NO 154
<211> LENGTH: 21
<212> TYPE: DNA
<213> ORGANISM: Artificial Sequence
<220> FEATURE:
<223> OTHER INFORMATION: target sequence

<400> SEQUENCE: 154
aaaattacag aatataaatt t                                              21

<210> SEQ ID NO 155
<211> LENGTH: 21
<212> TYPE: DNA
<213> ORGANISM: Artificial Sequence
<220> FEATURE:
<223> OTHER INFORMATION: target sequence

<400> SEQUENCE: 155
aaattacaga atataaattt g                                              21

<210> SEQ ID NO 156
<211> LENGTH: 21
<212> TYPE: DNA
<213> ORGANISM: Artificial Sequence
<220> FEATURE:
<223> OTHER INFORMATION: target sequence

<400> SEQUENCE: 156
aattacagaa tataaatttg g                                              21

<210> SEQ ID NO 157
<211> LENGTH: 21
<212> TYPE: DNA
<213> ORGANISM: Artificial Sequence
<220> FEATURE:
<223> OTHER INFORMATION: target sequence

<400> SEQUENCE: 157
aatataaatt tggcaatgtc t                                              21

<210> SEQ ID NO 158
<211> LENGTH: 21
<212> TYPE: DNA
<213> ORGANISM: Artificial Sequence
<220> FEATURE:
<223> OTHER INFORMATION: target sequence

<400> SEQUENCE: 158
aaatttggca atgtctccat t                                              21

<210> SEQ ID NO 159
<211> LENGTH: 21
<212> TYPE: DNA
<213> ORGANISM: Artificial Sequence

```
-continued

<220> FEATURE:
<223> OTHER INFORMATION: target sequence

<400> SEQUENCE: 159
aatttggcaa tgtctccatt a                                              21

<210> SEQ ID NO 160
<211> LENGTH: 21
<212> TYPE: DNA
<213> ORGANISM: Artificial Sequence
<220> FEATURE:
<223> OTHER INFORMATION: target sequence

<400> SEQUENCE: 160
aatgtctcca ttacccaccg c                                              21

<210> SEQ ID NO 161
<211> LENGTH: 21
<212> TYPE: DNA
<213> ORGANISM: Artificial Sequence
<220> FEATURE:
<223> OTHER INFORMATION: target sequence

<400> SEQUENCE: 161
aaacgccaaa gccacttcga a                                              21

<210> SEQ ID NO 162
<211> LENGTH: 21
<212> TYPE: DNA
<213> ORGANISM: Artificial Sequence
<220> FEATURE:
<223> OTHER INFORMATION: target sequence

<400> SEQUENCE: 162
aacgccaaag ccacttcgaa g                                              21

<210> SEQ ID NO 163
<211> LENGTH: 21
<212> TYPE: DNA
<213> ORGANISM: Artificial Sequence
<220> FEATURE:
<223> OTHER INFORMATION: target sequence

<400> SEQUENCE: 163
aaagccactt cgaagtagtg c                                              21

<210> SEQ ID NO 164
<211> LENGTH: 21
<212> TYPE: DNA
<213> ORGANISM: Artificial Sequence
<220> FEATURE:
<223> OTHER INFORMATION: target sequence

<400> SEQUENCE: 164
aagccacttc gaagtagtgc t                                              21

<210> SEQ ID NO 165
<211> LENGTH: 21
<212> TYPE: DNA
<213> ORGANISM: Artificial Sequence
<220> FEATURE:
<223> OTHER INFORMATION: target sequence

<400> SEQUENCE: 165
aagtagtgct gaccctgcac t                                              21
```

<210> SEQ ID NO 166
<211> LENGTH: 21
<212> TYPE: DNA
<213> ORGANISM: Artificial Sequence
<220> FEATURE:
<223> OTHER INFORMATION: target sequence

<400> SEQUENCE: 166
aatcaagaag ttgcattaaa a                                              21

<210> SEQ ID NO 167
<211> LENGTH: 21
<212> TYPE: DNA
<213> ORGANISM: Artificial Sequence
<220> FEATURE:
<223> OTHER INFORMATION: target sequence

<400> SEQUENCE: 167
aagaagttgc attaaaatta g                                              21

<210> SEQ ID NO 168
<211> LENGTH: 21
<212> TYPE: DNA
<213> ORGANISM: Artificial Sequence
<220> FEATURE:
<223> OTHER INFORMATION: target sequence

<400> SEQUENCE: 168
aagttgcatt aaaattagaa c                                              21

<210> SEQ ID NO 169
<211> LENGTH: 21
<212> TYPE: DNA
<213> ORGANISM: Artificial Sequence
<220> FEATURE:
<223> OTHER INFORMATION: target sequence

<400> SEQUENCE: 169
aaaattagaa ccaaatccag a                                              21

<210> SEQ ID NO 170
<211> LENGTH: 21
<212> TYPE: DNA
<213> ORGANISM: Artificial Sequence
<220> FEATURE:
<223> OTHER INFORMATION: target sequence

<400> SEQUENCE: 170
aaattagaac caaatccaga g                                              21

<210> SEQ ID NO 171
<211> LENGTH: 21
<212> TYPE: DNA
<213> ORGANISM: Artificial Sequence
<220> FEATURE:
<223> OTHER INFORMATION: target sequence

<400> SEQUENCE: 171
aattagaacc aaatccagag t                                              21

<210> SEQ ID NO 172
<211> LENGTH: 21
<212> TYPE: DNA
<213> ORGANISM: Artificial Sequence
<220> FEATURE:
<223> OTHER INFORMATION: target sequence

```
<400> SEQUENCE: 172
aaccaaatcc agagtcactg g                                              21

<210> SEQ ID NO 173
<211> LENGTH: 21
<212> TYPE: DNA
<213> ORGANISM: Artificial Sequence
<220> FEATURE:
<223> OTHER INFORMATION: target sequence

<400> SEQUENCE: 173
aaatccagag tcactggaac t                                              21

<210> SEQ ID NO 174
<211> LENGTH: 21
<212> TYPE: DNA
<213> ORGANISM: Artificial Sequence
<220> FEATURE:
<223> OTHER INFORMATION: target sequence

<400> SEQUENCE: 174
aatccagagt cactggaact t                                              21

<210> SEQ ID NO 175
<211> LENGTH: 21
<212> TYPE: DNA
<213> ORGANISM: Artificial Sequence
<220> FEATURE:
<223> OTHER INFORMATION: target sequence

<400> SEQUENCE: 175
aactttcttt taccatgccc c                                              21

<210> SEQ ID NO 176
<211> LENGTH: 21
<212> TYPE: DNA
<213> ORGANISM: Artificial Sequence
<220> FEATURE:
<223> OTHER INFORMATION: target sequence

<400> SEQUENCE: 176
aagcactaga caaagttcac c                                              21

<210> SEQ ID NO 177
<211> LENGTH: 21
<212> TYPE: DNA
<213> ORGANISM: Artificial Sequence
<220> FEATURE:
<223> OTHER INFORMATION: target sequence

<400> SEQUENCE: 177
aaagttcacc tgagcctaat a                                              21

<210> SEQ ID NO 178
<211> LENGTH: 21
<212> TYPE: DNA
<213> ORGANISM: Artificial Sequence
<220> FEATURE:
<223> OTHER INFORMATION: target sequence

<400> SEQUENCE: 178
aagttcacct gagcctaata g                                              21

<210> SEQ ID NO 179
```

```
<211> LENGTH: 21
<212> TYPE: DNA
<213> ORGANISM: Artificial Sequence
<220> FEATURE:
<223> OTHER INFORMATION: target sequence

<400> SEQUENCE: 179
aatagtccca gtgaatattg t                                              21

<210> SEQ ID NO 180
<211> LENGTH: 21
<212> TYPE: DNA
<213> ORGANISM: Artificial Sequence
<220> FEATURE:
<223> OTHER INFORMATION: target sequence

<400> SEQUENCE: 180
aatattgttt ttatgtggat a                                              21

<210> SEQ ID NO 181
<211> LENGTH: 21
<212> TYPE: DNA
<213> ORGANISM: Artificial Sequence
<220> FEATURE:
<223> OTHER INFORMATION: target sequence

<400> SEQUENCE: 181
aatgaattca agttggaatt g                                              21

<210> SEQ ID NO 182
<211> LENGTH: 21
<212> TYPE: DNA
<213> ORGANISM: Artificial Sequence
<220> FEATURE:
<223> OTHER INFORMATION: target sequence

<400> SEQUENCE: 182
aattcaagtt ggaattggta g                                              21

<210> SEQ ID NO 183
<211> LENGTH: 21
<212> TYPE: DNA
<213> ORGANISM: Artificial Sequence
<220> FEATURE:
<223> OTHER INFORMATION: target sequence

<400> SEQUENCE: 183
aagttggaat tggtagaaaa a                                              21

<210> SEQ ID NO 184
<211> LENGTH: 21
<212> TYPE: DNA
<213> ORGANISM: Artificial Sequence
<220> FEATURE:
<223> OTHER INFORMATION: target sequence

<400> SEQUENCE: 184
aattggtaga aaactttttt g                                              21

<210> SEQ ID NO 185
<211> LENGTH: 21
<212> TYPE: DNA
<213> ORGANISM: Artificial Sequence
<220> FEATURE:
<223> OTHER INFORMATION: target sequence

<400> SEQUENCE: 185
```

-continued

```
aaaactttttt gctgaagaca c                                              21

<210> SEQ ID NO 186
<211> LENGTH: 21
<212> TYPE: DNA
<213> ORGANISM: Artificial Sequence
<220> FEATURE:
<223> OTHER INFORMATION: target sequence

<400> SEQUENCE: 186 aaacttttg ctgaagacac a                                                21

<210> SEQ ID NO 187
<211> LENGTH: 21
<212> TYPE: DNA
<213> ORGANISM: Artificial Sequence
<220> FEATURE:
<223> OTHER INFORMATION: target sequence

<400> SEQUENCE: 187 aacttttgc tgaagacaca g                                                21

<210> SEQ ID NO 188
<211> LENGTH: 21
<212> TYPE: DNA
<213> ORGANISM: Artificial Sequence
<220> FEATURE:
<223> OTHER INFORMATION: target sequence

<400> SEQUENCE: 188
aagacacaga agcaaagaac c                                               21

<210> SEQ ID NO 189
<211> LENGTH: 21
<212> TYPE: DNA
<213> ORGANISM: Artificial Sequence
<220> FEATURE:
<223> OTHER INFORMATION: target sequence

<400> SEQUENCE: 189
aagcaaagaa cccattttct a                                               21

<210> SEQ ID NO 190
<211> LENGTH: 21
<212> TYPE: DNA
<213> ORGANISM: Artificial Sequence
<220> FEATURE:
<223> OTHER INFORMATION: target sequence

<400> SEQUENCE: 190
aaagaaccca ttttctactc a                                               21

<210> SEQ ID NO 191
<211> LENGTH: 21
<212> TYPE: DNA
<213> ORGANISM: Artificial Sequence
<220> FEATURE:
<223> OTHER INFORMATION: target sequence

<400> SEQUENCE: 191
aagaacccat tttctactca g                                               21

<210> SEQ ID NO 192
<211> LENGTH: 21
<212> TYPE: DNA
```

```
<213> ORGANISM: Artificial Sequence
<220> FEATURE:
<223> OTHER INFORMATION: target sequence

<400> SEQUENCE: 192
aacccatttt ctactcagga c                                              21

<210> SEQ ID NO 193
<211> LENGTH: 21
<212> TYPE: DNA
<213> ORGANISM: Artificial Sequence
<220> FEATURE:
<223> OTHER INFORMATION: target sequence

<400> SEQUENCE: 193
aatggatgat gacttccagt t                                              21

<210> SEQ ID NO 194
<211> LENGTH: 21
<212> TYPE: DNA
<213> ORGANISM: Artificial Sequence
<220> FEATURE:
<223> OTHER INFORMATION: target sequence

<400> SEQUENCE: 194
aaagcagttc cgcaagccct g                                              21

<210> SEQ ID NO 195
<211> LENGTH: 21
<212> TYPE: DNA
<213> ORGANISM: Artificial Sequence
<220> FEATURE:
<223> OTHER INFORMATION: target sequence

<400> SEQUENCE: 195
aagcagttcc gcaagccctg a                                              21

<210> SEQ ID NO 196
<211> LENGTH: 21
<212> TYPE: DNA
<213> ORGANISM: Artificial Sequence
<220> FEATURE:
<223> OTHER INFORMATION: target sequence

<400> SEQUENCE: 196
aagccctgaa agcgcaagtc c                                              21

<210> SEQ ID NO 197
<211> LENGTH: 21
<212> TYPE: DNA
<213> ORGANISM: Artificial Sequence
<220> FEATURE:
<223> OTHER INFORMATION: target sequence

<400> SEQUENCE: 197
aaagcgcaag tcctcaaagc a                                              21

<210> SEQ ID NO 198
<211> LENGTH: 21
<212> TYPE: DNA
<213> ORGANISM: Artificial Sequence
<220> FEATURE:
<223> OTHER INFORMATION: target sequence

<400> SEQUENCE: 198
aagcgcaagt cctcaaagca c                                              21
```

-continued

<210> SEQ ID NO 199
<211> LENGTH: 21
<212> TYPE: DNA
<213> ORGANISM: Artificial Sequence
<220> FEATURE:
<223> OTHER INFORMATION: target sequence

<400> SEQUENCE: 199
aagtcctcaa agcacagtta c                                              21

<210> SEQ ID NO 200
<211> LENGTH: 21
<212> TYPE: DNA
<213> ORGANISM: Artificial Sequence
<220> FEATURE:
<223> OTHER INFORMATION: target sequence

<400> SEQUENCE: 200
aaagcacagt tacagtattc c                                              21

<210> SEQ ID NO 201
<211> LENGTH: 21
<212> TYPE: DNA
<213> ORGANISM: Artificial Sequence
<220> FEATURE:
<223> OTHER INFORMATION: target sequence

<400> SEQUENCE: 201
aagcacagtt acagtattcc a                                              21

<210> SEQ ID NO 202
<211> LENGTH: 21
<212> TYPE: DNA
<213> ORGANISM: Artificial Sequence
<220> FEATURE:
<223> OTHER INFORMATION: target sequence

<400> SEQUENCE: 202
aaatacaaga acctactgct a                                              21

<210> SEQ ID NO 203
<211> LENGTH: 21
<212> TYPE: DNA
<213> ORGANISM: Artificial Sequence
<220> FEATURE:
<223> OTHER INFORMATION: target sequence

<400> SEQUENCE: 203
aatacaagaa cctactgcta a                                              21

<210> SEQ ID NO 204
<211> LENGTH: 21
<212> TYPE: DNA
<213> ORGANISM: Artificial Sequence
<220> FEATURE:
<223> OTHER INFORMATION: target sequence

<400> SEQUENCE: 204
aagaacctac tgctaatgcc a                                              21

<210> SEQ ID NO 205
<211> LENGTH: 21
<212> TYPE: DNA
<213> ORGANISM: Artificial Sequence
<220> FEATURE:

<223> OTHER INFORMATION: target sequence

<400> SEQUENCE: 205
aacctactgc taatgccacc a                                              21

<210> SEQ ID NO 206
<211> LENGTH: 21
<212> TYPE: DNA
<213> ORGANISM: Artificial Sequence
<220> FEATURE:
<223> OTHER INFORMATION: target sequence

<400> SEQUENCE: 206
aatgccacca ctaccactgc c                                              21

<210> SEQ ID NO 207
<211> LENGTH: 21
<212> TYPE: DNA
<213> ORGANISM: Artificial Sequence
<220> FEATURE:
<223> OTHER INFORMATION: target sequence

<400> SEQUENCE: 207
aattaaaaac agtgacaaaa g                                              21

<210> SEQ ID NO 208
<211> LENGTH: 21
<212> TYPE: DNA
<213> ORGANISM: Artificial Sequence
<220> FEATURE:
<223> OTHER INFORMATION: target sequence

<400> SEQUENCE: 208
aaaaacagtg acaaaagacc g                                              21

<210> SEQ ID NO 209
<211> LENGTH: 21
<212> TYPE: DNA
<213> ORGANISM: Artificial Sequence
<220> FEATURE:
<223> OTHER INFORMATION: target sequence

<400> SEQUENCE: 209
aaaacagtga caaaagaccg t                                              21

<210> SEQ ID NO 210
<211> LENGTH: 21
<212> TYPE: DNA
<213> ORGANISM: Artificial Sequence
<220> FEATURE:
<223> OTHER INFORMATION: target sequence

<400> SEQUENCE: 210
aaacagtgac aaaagaccgt a                                              21

<210> SEQ ID NO 211
<211> LENGTH: 21
<212> TYPE: DNA
<213> ORGANISM: Artificial Sequence
<220> FEATURE:
<223> OTHER INFORMATION: target sequence

<400> SEQUENCE: 211
aacagtgaca aaagaccgta t                                              21

<210> SEQ ID NO 212
<211> LENGTH: 21
<212> TYPE: DNA
<213> ORGANISM: Artificial Sequence
<220> FEATURE:
<223> OTHER INFORMATION: target sequence

<400> SEQUENCE: 212
aaaagaccgt atggaagaca t                                    21

<210> SEQ ID NO 213
<211> LENGTH: 21
<212> TYPE: DNA
<213> ORGANISM: Artificial Sequence
<220> FEATURE:
<223> OTHER INFORMATION: target sequence

<400> SEQUENCE: 213
aaagaccgta tggaagacat t                                    21

<210> SEQ ID NO 214
<211> LENGTH: 21
<212> TYPE: DNA
<213> ORGANISM: Artificial Sequence
<220> FEATURE:
<223> OTHER INFORMATION: target sequence

<400> SEQUENCE: 214
aagaccgtat ggaagacatt a                                    21

<210> SEQ ID NO 215
<211> LENGTH: 21
<212> TYPE: DNA
<213> ORGANISM: Artificial Sequence
<220> FEATURE:
<223> OTHER INFORMATION: target sequence

<400> SEQUENCE: 215
aagacattaa aatattgatt g                                    21

<210> SEQ ID NO 216
<211> LENGTH: 21
<212> TYPE: DNA
<213> ORGANISM: Artificial Sequence
<220> FEATURE:
<223> OTHER INFORMATION: target sequence

<400> SEQUENCE: 216
aaaatattga ttgcatctcc a                                    21

<210> SEQ ID NO 217
<211> LENGTH: 21
<212> TYPE: DNA
<213> ORGANISM: Artificial Sequence
<220> FEATURE:
<223> OTHER INFORMATION: target sequence

<400> SEQUENCE: 217
aaatattgat tgcatctcca t                                    21

<210> SEQ ID NO 218
<211> LENGTH: 21
<212> TYPE: DNA
<213> ORGANISM: Artificial Sequence
<220> FEATURE:
<223> OTHER INFORMATION: target sequence

<400> SEQUENCE: 218
aatattgatt gcatctccat c                                        21

<210> SEQ ID NO 219
<211> LENGTH: 21
<212> TYPE: DNA
<213> ORGANISM: Artificial Sequence
<220> FEATURE:
<223> OTHER INFORMATION: target sequence

<400> SEQUENCE: 219
aaagaaacta ctagtgccac a                                        21

<210> SEQ ID NO 220
<211> LENGTH: 21
<212> TYPE: DNA
<213> ORGANISM: Artificial Sequence
<220> FEATURE:
<223> OTHER INFORMATION: target sequence

<400> SEQUENCE: 220
aagaaactac tagtgccaca t                                        21

<210> SEQ ID NO 221
<211> LENGTH: 21
<212> TYPE: DNA
<213> ORGANISM: Artificial Sequence
<220> FEATURE:
<223> OTHER INFORMATION: target sequence

<400> SEQUENCE: 221
aaactactag tgccacatca t                                        21

<210> SEQ ID NO 222
<211> LENGTH: 21
<212> TYPE: DNA
<213> ORGANISM: Artificial Sequence
<220> FEATURE:
<223> OTHER INFORMATION: target sequence

<400> SEQUENCE: 222
aactactagt gccacatcat c                                        21

<210> SEQ ID NO 223
<211> LENGTH: 21
<212> TYPE: DNA
<213> ORGANISM: Artificial Sequence
<220> FEATURE:
<223> OTHER INFORMATION: target sequence

<400> SEQUENCE: 223
aaagtcggac agcctcacca a                                        21

<210> SEQ ID NO 224
<211> LENGTH: 21
<212> TYPE: DNA
<213> ORGANISM: Artificial Sequence
<220> FEATURE:
<223> OTHER INFORMATION: target sequence

<400> SEQUENCE: 224
aagtcggaca gcctcaccaa a                                        21

<210> SEQ ID NO 225
<211> LENGTH: 21

-continued

```
<212> TYPE: DNA
<213> ORGANISM: Artificial Sequence
<220> FEATURE:
<223> OTHER INFORMATION: target sequence

<400> SEQUENCE: 225
aaacagagca ggaaaaggag t                                               21

<210> SEQ ID NO 226
<211> LENGTH: 21
<212> TYPE: DNA
<213> ORGANISM: Artificial Sequence
<220> FEATURE:
<223> OTHER INFORMATION: target sequence

<400> SEQUENCE: 226
aacagagcag gaaaaggagt c                                               21

<210> SEQ ID NO 227
<211> LENGTH: 21
<212> TYPE: DNA
<213> ORGANISM: Artificial Sequence
<220> FEATURE:
<223> OTHER INFORMATION: target sequence

<400> SEQUENCE: 227
aaaaggagtc atagaacaga c                                               21

<210> SEQ ID NO 228
<211> LENGTH: 21
<212> TYPE: DNA
<213> ORGANISM: Artificial Sequence
<220> FEATURE:
<223> OTHER INFORMATION: target sequence

<400> SEQUENCE: 228
aaaggagtca tagaacagac a                                               21

<210> SEQ ID NO 229
<211> LENGTH: 21
<212> TYPE: DNA
<213> ORGANISM: Artificial Sequence
<220> FEATURE:
<223> OTHER INFORMATION: target sequence

<400> SEQUENCE: 229
aaggagtcat agaacagaca g                                               21

<210> SEQ ID NO 230
<211> LENGTH: 21
<212> TYPE: DNA
<213> ORGANISM: Artificial Sequence
<220> FEATURE:
<223> OTHER INFORMATION: target sequence

<400> SEQUENCE: 230
aacagacaga aaatctcat c                                                21

<210> SEQ ID NO 231
<211> LENGTH: 21
<212> TYPE: DNA
<213> ORGANISM: Artificial Sequence
<220> FEATURE:
<223> OTHER INFORMATION: target sequence

<400> SEQUENCE: 231
```

-continued

| aaaaatctca tccaagaagc c | 21 |

<210> SEQ ID NO 232
<211> LENGTH: 21
<212> TYPE: DNA
<213> ORGANISM: Artificial Sequence
<220> FEATURE:
<223> OTHER INFORMATION: target sequence

<400> SEQUENCE: 232

| aaaatctcat ccaagaagcc c | 21 |

<210> SEQ ID NO 233
<211> LENGTH: 21
<212> TYPE: DNA
<213> ORGANISM: Artificial Sequence
<220> FEATURE:
<223> OTHER INFORMATION: target sequence

<400> SEQUENCE: 233

| aaatctcatc caagaagccc t | 21 |

<210> SEQ ID NO 234
<211> LENGTH: 21
<212> TYPE: DNA
<213> ORGANISM: Artificial Sequence
<220> FEATURE:
<223> OTHER INFORMATION: target sequence

<400> SEQUENCE: 234

| aatctcatcc aagaagccct a | 21 |

<210> SEQ ID NO 235
<211> LENGTH: 21
<212> TYPE: DNA
<213> ORGANISM: Artificial Sequence
<220> FEATURE:
<223> OTHER INFORMATION: target sequence

<400> SEQUENCE: 235

| aagaagccct aacgtgttat c | 21 |

<210> SEQ ID NO 236
<211> LENGTH: 21
<212> TYPE: DNA
<213> ORGANISM: Artificial Sequence
<220> FEATURE:
<223> OTHER INFORMATION: target sequence

<400> SEQUENCE: 236

| aagccctaac gtgttatctg t | 21 |

<210> SEQ ID NO 237
<211> LENGTH: 21
<212> TYPE: DNA
<213> ORGANISM: Artificial Sequence
<220> FEATURE:
<223> OTHER INFORMATION: target sequence

<400> SEQUENCE: 237

| aacgtgttat ctgtcgcttt g | 21 |

<210> SEQ ID NO 238
<211> LENGTH: 21
<212> TYPE: DNA
<213> ORGANISM: Artificial Sequence

```
<220> FEATURE:
<223> OTHER INFORMATION: target sequence

<400> SEQUENCE: 238
aaagaactac agttcctgag g                                            21

<210> SEQ ID NO 239
<211> LENGTH: 21
<212> TYPE: DNA
<213> ORGANISM: Artificial Sequence
<220> FEATURE:
<223> OTHER INFORMATION: target sequence

<400> SEQUENCE: 239
aagaactaca gttcctgagg a                                            21

<210> SEQ ID NO 240
<211> LENGTH: 21
<212> TYPE: DNA
<213> ORGANISM: Artificial Sequence
<220> FEATURE:
<223> OTHER INFORMATION: target sequence

<400> SEQUENCE: 240
aactacagtt cctgaggaag a                                            21

<210> SEQ ID NO 241
<211> LENGTH: 21
<212> TYPE: DNA
<213> ORGANISM: Artificial Sequence
<220> FEATURE:
<223> OTHER INFORMATION: target sequence

<400> SEQUENCE: 241
aagaactaaa tccaaagata c                                            21

<210> SEQ ID NO 242
<211> LENGTH: 21
<212> TYPE: DNA
<213> ORGANISM: Artificial Sequence
<220> FEATURE:
<223> OTHER INFORMATION: target sequence

<400> SEQUENCE: 242
aactaaatcc aaagatacta g                                            21

<210> SEQ ID NO 243
<211> LENGTH: 21
<212> TYPE: DNA
<213> ORGANISM: Artificial Sequence
<220> FEATURE:
<223> OTHER INFORMATION: target sequence

<400> SEQUENCE: 243
aaatccaaag atactagctt t                                            21

<210> SEQ ID NO 244
<211> LENGTH: 21
<212> TYPE: DNA
<213> ORGANISM: Artificial Sequence
<220> FEATURE:
<223> OTHER INFORMATION: target sequence

<400> SEQUENCE: 244
aatccaaaga tactagcttt g                                            21
```

<210> SEQ ID NO 245
<211> LENGTH: 21
<212> TYPE: DNA
<213> ORGANISM: Artificial Sequence
<220> FEATURE:
<223> OTHER INFORMATION: target sequence

<400> SEQUENCE: 245
aaagatacta gctttgcaga a                                              21

<210> SEQ ID NO 246
<211> LENGTH: 21
<212> TYPE: DNA
<213> ORGANISM: Artificial Sequence
<220> FEATURE:
<223> OTHER INFORMATION: target sequence

<400> SEQUENCE: 246
aagatactag ctttgcagaa t                                              21

<210> SEQ ID NO 247
<211> LENGTH: 21
<212> TYPE: DNA
<213> ORGANISM: Artificial Sequence
<220> FEATURE:
<223> OTHER INFORMATION: target sequence

<400> SEQUENCE: 247
aatgctcaga gaaagcgaaa a                                              21

<210> SEQ ID NO 248
<211> LENGTH: 21
<212> TYPE: DNA
<213> ORGANISM: Artificial Sequence
<220> FEATURE:
<223> OTHER INFORMATION: target sequence

<400> SEQUENCE: 248
aaagcgaaaa atggaacatg a                                              21

<210> SEQ ID NO 249
<211> LENGTH: 21
<212> TYPE: DNA
<213> ORGANISM: Artificial Sequence
<220> FEATURE:
<223> OTHER INFORMATION: target sequence

<400> SEQUENCE: 249
aagcgaaaaa tggaacatga t                                              21

<210> SEQ ID NO 250
<211> LENGTH: 21
<212> TYPE: DNA
<213> ORGANISM: Artificial Sequence
<220> FEATURE:
<223> OTHER INFORMATION: target sequence

<400> SEQUENCE: 250
aaaaatggaa catgatggtt c                                              21

<210> SEQ ID NO 251
<211> LENGTH: 21
<212> TYPE: DNA
<213> ORGANISM: Artificial Sequence
<220> FEATURE:
<223> OTHER INFORMATION: target sequence

<400> SEQUENCE: 251
aaaatggaac atgatggttc a                                               21

<210> SEQ ID NO 252
<211> LENGTH: 21
<212> TYPE: DNA
<213> ORGANISM: Artificial Sequence
<220> FEATURE:
<223> OTHER INFORMATION: target sequence

<400> SEQUENCE: 252
aaatggaaca tgatggttca c                                               21

<210> SEQ ID NO 253
<211> LENGTH: 21
<212> TYPE: DNA
<213> ORGANISM: Artificial Sequence
<220> FEATURE:
<223> OTHER INFORMATION: target sequence

<400> SEQUENCE: 253
aatggaacat gatggttcac t                                               21

<210> SEQ ID NO 254
<211> LENGTH: 21
<212> TYPE: DNA
<213> ORGANISM: Artificial Sequence
<220> FEATURE:
<223> OTHER INFORMATION: target sequence

<400> SEQUENCE: 254
aacatgatgg ttcactttt c                                                21

<210> SEQ ID NO 255
<211> LENGTH: 21
<212> TYPE: DNA
<213> ORGANISM: Artificial Sequence
<220> FEATURE:
<223> OTHER INFORMATION: target sequence

<400> SEQUENCE: 255
aagcagtagg aattggaaca t                                               21

<210> SEQ ID NO 256
<211> LENGTH: 21
<212> TYPE: DNA
<213> ORGANISM: Artificial Sequence
<220> FEATURE:
<223> OTHER INFORMATION: target sequence

<400> SEQUENCE: 256
aattggaaca ttattacagc a                                               21

<210> SEQ ID NO 257
<211> LENGTH: 21
<212> TYPE: DNA
<213> ORGANISM: Artificial Sequence
<220> FEATURE:
<223> OTHER INFORMATION: target sequence

<400> SEQUENCE: 257
aacattatta cagcagccag a                                               21

<210> SEQ ID NO 258

```
<211> LENGTH: 21
<212> TYPE: DNA
<213> ORGANISM: Artificial Sequence
<220> FEATURE:
<223> OTHER INFORMATION: target sequence

<400> SEQUENCE: 258
aaacgtgtaa aaggatgcaa a                                              21

<210> SEQ ID NO 259
<211> LENGTH: 21
<212> TYPE: DNA
<213> ORGANISM: Artificial Sequence
<220> FEATURE:
<223> OTHER INFORMATION: target sequence

<400> SEQUENCE: 259
aacgtgtaaa aggatgcaaa t                                              21

<210> SEQ ID NO 260
<211> LENGTH: 21
<212> TYPE: DNA
<213> ORGANISM: Artificial Sequence
<220> FEATURE:
<223> OTHER INFORMATION: target sequence

<400> SEQUENCE: 260
aaaaggatgc aaatctagtg a                                              21

<210> SEQ ID NO 261
<211> LENGTH: 21
<212> TYPE: DNA
<213> ORGANISM: Artificial Sequence
<220> FEATURE:
<223> OTHER INFORMATION: target sequence

<400> SEQUENCE: 261
aaaggatgca aatctagtga a                                              21

<210> SEQ ID NO 262
<211> LENGTH: 21
<212> TYPE: DNA
<213> ORGANISM: Artificial Sequence
<220> FEATURE:
<223> OTHER INFORMATION: target sequence

<400> SEQUENCE: 262
aaggatgcaa atctagtgaa c                                              21

<210> SEQ ID NO 263
<211> LENGTH: 21
<212> TYPE: DNA
<213> ORGANISM: Artificial Sequence
<220> FEATURE:
<223> OTHER INFORMATION: target sequence

<400> SEQUENCE: 263
aaatctagtg aacagaatgg a                                              21

<210> SEQ ID NO 264
<211> LENGTH: 21
<212> TYPE: DNA
<213> ORGANISM: Artificial Sequence
<220> FEATURE:
<223> OTHER INFORMATION: target sequence

<400> SEQUENCE: 264
```
aatctagtga acagaatgga a                                    21

<210> SEQ ID NO 265
<211> LENGTH: 21
<212> TYPE: DNA
<213> ORGANISM: Artificial Sequence
<220> FEATURE:
<223> OTHER INFORMATION: target sequence

<400> SEQUENCE: 265
aacagaatgg aatggagcaa a                                    21

<210> SEQ ID NO 266
<211> LENGTH: 21
<212> TYPE: DNA
<213> ORGANISM: Artificial Sequence
<220> FEATURE:
<223> OTHER INFORMATION: target sequence

<400> SEQUENCE: 266
aatggaatgg agcaaaagac a                                    21

<210> SEQ ID NO 267
<211> LENGTH: 21
<212> TYPE: DNA
<213> ORGANISM: Artificial Sequence
<220> FEATURE:
<223> OTHER INFORMATION: target sequence

<400> SEQUENCE: 267
aatggagcaa aagacaatta t                                    21

<210> SEQ ID NO 268
<211> LENGTH: 21
<212> TYPE: DNA
<213> ORGANISM: Artificial Sequence
<220> FEATURE:
<223> OTHER INFORMATION: target sequence

<400> SEQUENCE: 268
aaaagacaat tattttaata c                                    21

<210> SEQ ID NO 269
<211> LENGTH: 21
<212> TYPE: DNA
<213> ORGANISM: Artificial Sequence
<220> FEATURE:
<223> OTHER INFORMATION: target sequence

<400> SEQUENCE: 269
aaagacaatt attttaatac c                                    21

<210> SEQ ID NO 270
<211> LENGTH: 21
<212> TYPE: DNA
<213> ORGANISM: Artificial Sequence
<220> FEATURE:
<223> OTHER INFORMATION: target sequence

<400> SEQUENCE: 270
aagacaatta ttttaatacc c                                    21

<210> SEQ ID NO 271
<211> LENGTH: 21
<212> TYPE: DNA

-continued

```
<213> ORGANISM: Artificial Sequence
<220> FEATURE:
<223> OTHER INFORMATION: target sequence

<400> SEQUENCE: 271
aattatttta ataccctctg a                                              21

<210> SEQ ID NO 272
<211> LENGTH: 21
<212> TYPE: DNA
<213> ORGANISM: Artificial Sequence
<220> FEATURE:
<223> OTHER INFORMATION: target sequence

<400> SEQUENCE: 272 aatacccctct gatttagcat g                                             21

<210> SEQ ID NO 273
<211> LENGTH: 21
<212> TYPE: DNA
<213> ORGANISM: Artificial Sequence
<220> FEATURE:
<223> OTHER INFORMATION: target sequence

<400> SEQUENCE: 273
aatcaatgga tgaaagtgga t                                              21

<210> SEQ ID NO 274
<211> LENGTH: 21
<212> TYPE: DNA
<213> ORGANISM: Artificial Sequence
<220> FEATURE:
<223> OTHER INFORMATION: target sequence

<400> SEQUENCE: 274
aatggatgaa agtggattac c                                              21

<210> SEQ ID NO 275
<211> LENGTH: 21
<212> TYPE: DNA
<213> ORGANISM: Artificial Sequence
<220> FEATURE:
<223> OTHER INFORMATION: target sequence

<400> SEQUENCE: 275
aaagtggatt accacagctg a                                              21

<210> SEQ ID NO 276
<211> LENGTH: 21
<212> TYPE: DNA
<213> ORGANISM: Artificial Sequence
<220> FEATURE:
<223> OTHER INFORMATION: target sequence

<400> SEQUENCE: 276
aagtggatta ccacagctga c                                              21

<210> SEQ ID NO 277
<211> LENGTH: 21
<212> TYPE: DNA
<213> ORGANISM: Artificial Sequence
<220> FEATURE:
<223> OTHER INFORMATION: target sequence

<400> SEQUENCE: 277
catcagttgc cacttccaca t                                              21
```

<210> SEQ ID NO 278
<211> LENGTH: 21
<212> TYPE: DNA
<213> ORGANISM: Artificial Sequence
<220> FEATURE:
<223> OTHER INFORMATION: target sequence

<400> SEQUENCE: 278
cttggatggt tttgttatgg t                                        21

<210> SEQ ID NO 279
<211> LENGTH: 21
<212> TYPE: DNA
<213> ORGANISM: Artificial Sequence
<220> FEATURE:
<223> OTHER INFORMATION: target sequence

<400> SEQUENCE: 279
atgggattaa ctcagtttga a                                        21

<210> SEQ ID NO 280
<211> LENGTH: 21
<212> TYPE: DNA
<213> ORGANISM: Artificial Sequence
<220> FEATURE:
<223> OTHER INFORMATION: target sequence

<400> SEQUENCE: 280
gtctgcaaca tggaaggtat t                                        21

<210> SEQ ID NO 281
<211> LENGTH: 21
<212> TYPE: DNA
<213> ORGANISM: Artificial Sequence
<220> FEATURE:
<223> OTHER INFORMATION: target sequence

<400> SEQUENCE: 281
cattcctcac ccatcaaata t                                        21

<210> SEQ ID NO 282
<211> LENGTH: 21
<212> TYPE: DNA
<213> ORGANISM: Artificial Sequence
<220> FEATURE:
<223> OTHER INFORMATION: target sequence

<400> SEQUENCE: 282
aggccgctca atttatgaat a                                        21

<210> SEQ ID NO 283
<211> LENGTH: 21
<212> TYPE: DNA
<213> ORGANISM: Artificial Sequence
<220> FEATURE:
<223> OTHER INFORMATION: target sequence

<400> SEQUENCE: 283
tcatatataa caccaagaat t                                        21

<210> SEQ ID NO 284
<211> LENGTH: 21
<212> TYPE: DNA
<213> ORGANISM: Artificial Sequence
<220> FEATURE:

```
<223> OTHER INFORMATION: target sequence

<400> SEQUENCE: 284
tgtccttaaa ccggttgaat c                                              21

<210> SEQ ID NO 285
<211> LENGTH: 21
<212> TYPE: DNA
<213> ORGANISM: Artificial Sequence
<220> FEATURE:
<223> OTHER INFORMATION: target sequence

<400> SEQUENCE: 285
agcctctttg acaaacttaa g                                              21

<210> SEQ ID NO 286
<211> LENGTH: 21
<212> TYPE: DNA
<213> ORGANISM: Artificial Sequence
<220> FEATURE:
<223> OTHER INFORMATION: target sequence

<400> SEQUENCE: 286
atgaccagca acttgaggaa g                                              21

<210> SEQ ID NO 287
<211> LENGTH: 21
<212> TYPE: DNA
<213> ORGANISM: Artificial Sequence
<220> FEATURE:
<223> OTHER INFORMATION: target sequence

<400> SEQUENCE: 287
cattacccac cgctgaaacg c                                              21

<210> SEQ ID NO 288
<211> LENGTH: 21
<212> TYPE: DNA
<213> ORGANISM: Artificial Sequence
<220> FEATURE:
<223> OTHER INFORMATION: target sequence

<400> SEQUENCE: 288
agattcagga tcagacacct a                                              21

<210> SEQ ID NO 289
<211> LENGTH: 21
<212> TYPE: DNA
<213> ORGANISM: Artificial Sequence
<220> FEATURE:
<223> OTHER INFORMATION: target sequence

<400> SEQUENCE: 289
atagtgatat ggtcaatgaa t                                              21

<210> SEQ ID NO 290
<211> LENGTH: 21
<212> TYPE: DNA
<213> ORGANISM: Artificial Sequence
<220> FEATURE:
<223> OTHER INFORMATION: target sequence

<400> SEQUENCE: 290
acacagattt agacttggag a                                              21
```

```
<210> SEQ ID NO 291
<211> LENGTH: 21
<212> TYPE: DNA
<213> ORGANISM: Artificial Sequence
<220> FEATURE:
<223> OTHER INFORMATION: target sequence

<400> SEQUENCE: 291
cacagttaca gtattccagc a                                              21

<210> SEQ ID NO 292
<211> LENGTH: 21
<212> TYPE: DNA
<213> ORGANISM: Artificial Sequence
<220> FEATURE:
<223> OTHER INFORMATION: target sequence

<400> SEQUENCE: 292
attgattgca tctccatctc c                                              21

<210> SEQ ID NO 293
<211> LENGTH: 21
<212> TYPE: DNA
<213> ORGANISM: Artificial Sequence
<220> FEATURE:
<223> OTHER INFORMATION: target sequence

<400> SEQUENCE: 293
atactagctt tgcagaatgc t                                              21

<210> SEQ ID NO 294
<211> LENGTH: 21
<212> TYPE: DNA
<213> ORGANISM: Artificial Sequence
<220> FEATURE:
<223> OTHER INFORMATION: target sequence

<400> SEQUENCE: 294
attattacag cagccagacg a                                              21

<210> SEQ ID NO 295
<211> LENGTH: 21
<212> TYPE: DNA
<213> ORGANISM: Artificial Sequence
<220> FEATURE:
<223> OTHER INFORMATION: target sequence

<400> SEQUENCE: 295
acaattattt taatccctc t                                               21

<210> SEQ ID NO 296
<211> LENGTH: 21
<212> TYPE: DNA
<213> ORGANISM: Artificial Sequence
<220> FEATURE:
<223> OTHER INFORMATION: target sequence

<400> SEQUENCE: 296
accagttatg attgtgaagt t                                              21

<210> SEQ ID NO 297
<211> LENGTH: 21
<212> TYPE: DNA
<213> ORGANISM: Artificial Sequence
<220> FEATURE:
<223> OTHER INFORMATION: target sequence
```

```
-continued

<400> SEQUENCE: 297
aactaactgg acacagtgtg t                                               21

<210> SEQ ID NO 298
<211> LENGTH: 21
<212> TYPE: DNA
<213> ORGANISM: Artificial Sequence
<220> FEATURE:
<223> OTHER INFORMATION: siRNA sense strand

<400> SEQUENCE: 298
cuaacuggac acagugugut t                                               21

<210> SEQ ID NO 299
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 299
acacacugug uccaguuagt t                                               21
```

COMPOSITIONS AND METHODS FOR SIRNA INHIBITION OF HIF-1 ALPHA

CROSS REFERENCE TO RELATED APPLICATION

This application claims the benefit of U.S. provisional patent application Ser. No. 60/423,262, filed on Nov. 1, 2002.

FIELD OF THE INVENTION

This invention relates to the regulation of gene expression by siRNA-induced degradation of the transcriptional regulator HIF-1 alpha. In particular, genes in the VEGF mitogenic pathway can be down-regulated.

BACKGROUND OF THE INVENTION

Angiogenesis, defined as the growth of new capillary blood vessels, plays a fundamental role in growth and development. In mature humans, the ability to initiate an angiogenic response is present in all tissues, but is held under strict control. A key regulator of angiogenesis is vascular endothelial growth factor ("VEGF"), also called vascular permeability factor ("VPF").

VEGF is expressed in abnormally high levels in certain tissues from diseases characterized by aberrant angiogenesis, such as cancers, diabetic retinopathy, psoriasis, age-related macular degeneration, rheumatoid arthritis and other inflammatory diseases. Therefore, agents which selectively decrease the VEGF levels in these tissues can be used to treat cancer and other angiogenic diseases.

Hypoxia-inducible factor 1 (HIF-1) is a heterodimeric basic-helix-loop-helix-PAS transcription factor consisting of HIF-1 alpha and HIF-1 beta subunits. HIF-1 alpha expression and HIF-1 transcriptional activity increase exponentially as cellular oxygen concentration is decreased. Several dozen target genes that are transactivated by HIF-1 have been identified, including those encoding erythropoietin, glucose transporters, glycolytic enzymes, and VEGF. Semenza G L (1999), *Ann. Rev. Cell. Dev. Biol.* 15: 551-578.

Loss of p53 in tumor cells enhances HIF-1 alpha levels and augments HIF-1-dependent transcriptional activation of VEGF in response to hypoxia. Forced expression of HIF-1 alpha in p53-expressing tumor cells increases hypoxia-induced VEGF expression and augments neovascularization and growth of tumor xenografts. These results indicate that amplification of normal HIF-1-dependent responses to hypoxia via loss of p53 function contributes to the angiogenic switch during tumorigenesis. Ravi R. et al. (2000), *Genes Dev.* 14: 34-44.

RNA interference ("RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), *Nature* 391: 806-811). These short dsRNA molecules, called "short interfering RNA" or "siRNA," cause the destruction of messenger RNAs ("mRNAs") which share sequence homology with the siRNA to within one nucleotide resolution (Elbashir S M et al. (2001), *Genes Dev*, 15: 188-200). It is believed that the siRNA and the targeted mRNA bind to an RNA-induced silencing complex ("RISC"), which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi is therefore more effective than other currently available technologies for inhibiting expression of a target gene.

Elbashir S M et al. (2001), supra, has shown that synthetic siRNA of 21 and 22 nucleotides in length, and which have short 3' overhangs, can induce RNAi of target mRNA in a Drosophila cell lysate. Cultured mammalian cells also exhibit RNAi with synthetic siRNA (Elbashir S M et al. (2001) *Nature*, 411: 494-498), and RNAi induced by synthetic siRNA has recently been shown in living mice (McCaffrey A P et al. (2002), *Nature*, 418: 38-39; Xia H et al. (2002), *Nat. Biotech.* 20: 1006-1010). The therapeutic potential of siRNA-mediated RNAi has been demonstrated by several recent in vitro studies, including the siRNA-directed inhibition of HIV-1 infection (Novina C D et al. (2002), *Nat. Med.* 8: 681-686) and reduction of neurotoxic polyglutamine disease protein expression (Xia H et al. (2002), supra). Therapeutic RNAi has also been demonstrated in human cancer cells by Alan Gewirtz, as described in published U.S. patent application US 2002/0173478.

It has now been found that siRNA-induced RNAi of HIF-1 alpha results in the destruction of HIF-1 alpha mRNA, with a concomitant reduction in VEGF expression and inhibition of angiogenesis.

SUMMARY OF THE INVENTION

The present invention is directed to siRNAs which specifically target and cause RNAi-induced degradation of mRNA from the human HIF-1 alpha gene. The siRNA compounds and compositions of the invention are used to treat cancerous tumors and other angiogenic diseases and non-pathogenic conditions in which VEGF is overexpressed in tissues in or near the area of neovascularization.

Thus, the invention provides siRNA, and pharmaceutical compositions thereof, which target HIF-1 alpha mRNA and induce RNAi-mediated degradation of the targeted mRNA.

The invention further provides a method of inhibiting expression of HIF-1 alpha, comprising administering to a subject an effective amount of an siRNA targeted to HIF-1 alpha mRNA, such that the HIF-1 alpha mRNA is degraded.

The invention further provides a method of inhibiting angiogenesis, comprising administering an effective amount of an siRNA targeted to HIF-1 alpha mRNA to a subject, such that the HIF-1 alpha mRNA is degraded and the expression of VEGF is inhibited.

The invention further provides a method of treating an angiogenic disease, comprising administering an effective amount of an siRNA targeted to HIF-1 alpha mRNA to a subject, such that the HIF-1 alpha mRNA is degraded and the expression of VEGF is inhibited.

DETAILED DESCRIPTION OF THE INVENTION

Figure 1:
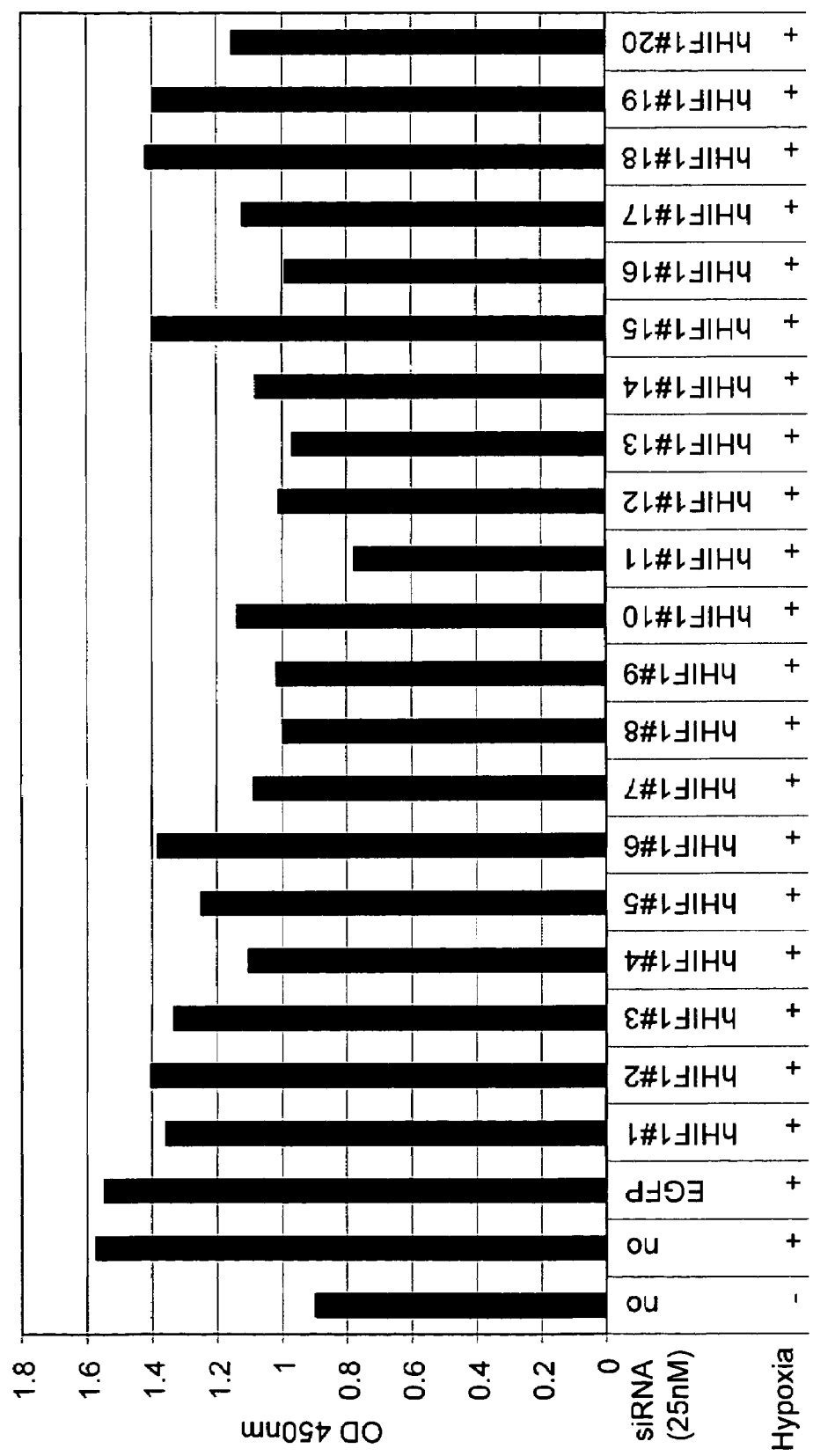
FIG. 1 is a histogram of VEGF concentration, as measured by VEGF ELISA at $OD_{450}$ nanometers, in non-hypoxic ("−") cultured HEK-293 cells treated with no siRNA ("no"), and in hypoxic ("+") cultured HEK-293 cells treated with: no siRNA ("no"); nonspecific siRNA ("EGFP"); or with twenty separate siRNAs targeting human HIF-1 alpha mRNA ("hHIF1#1-20").

Compositions and methods comprising siRNA targeted to HIF-1 alpha mRNA are advantageously used to inhibit angiogenesis, in particular for the treatment of angiogenic diseases. The siRNA of the invention causes RNAi-mediated destruction of the HIF-1 alpha mRNA. HIF-1 alpha is a transcriptional regulator of VEGF, and the reduction in HIF-1 alpha mRNA caused by the siRNA of the invention is correlated with a reduction in VEGF production. Because VEGF is required for initiating and maintaining angiogenesis, the siRNA-mediated destruction of HIF-1 alpha slows, stops or reverses the angiogenic process.

As used herein, siRNA which is "targeted to the HIF-1 alpha mRNA" means siRNA in which a first strand of the duplex has the same nucleotide sequence as a portion of the HIF-1 mRNA sequence. It is understood that the second strand of the siRNA duplex is complementary to both the first strand of the siRNA duplex and to the same portion of the HIF-1 alpha mRNA.

The invention therefore provides isolated siRNA comprising short double-stranded RNA from about 17 nucleotides to about 29 nucleotides in length, preferably from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is substantially identical to a target sequence contained within the target mRNA.

As used herein, a nucleic acid sequence "substantially identical" to a target sequence contained within the target mRNA is a nucleic acid sequence which is identical to the target sequence, or which differs from the target sequence by one or more nucleotides. Sense strands of the invention which comprise nucleic acid sequences substantially identical to a target sequence are characterized in that siRNA comprising such sense strands induce RNAi-mediated degradation of mRNA containing the target sequence. For example, an siRNA of the invention can comprise a sense strand comprise nucleic acid sequences which differ from a target sequence by one, two or three or more nucleotides, as long as RNAi-mediated degradation of the target mRNA is induced by the siRNA.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules (see Tuschl, T. (2002), supra). As described below, the siRNA can also contain alterations, substitutions or modifications of one or more ribonucleotide bases. For example, the present siRNA can be altered, substituted or modified to contain one or more deoxyribonucleotide bases.

As used herein, "isolated" means synthetic, or altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

As used herein, "target mRNA" means human HIF-1 alpha mRNA, mutant or alternative splice forms of human HIF-1 alpha mRNA, or mRNA from cognate HIF-1 alpha genes. A cDNA sequence corresponding to a human HIF-1 alpha mRNA sequence is given in SEQ ID NO: 1.

Splice variants of human HIF-1 alpha are known, including HIF-1 alpha transcript variants 1 (SEQ ID NO: 2) and 2 (SEQ ID NO: 3), as described in GenBank record accession nos. NM_001530 and NM_181054, the entire disclosures of which are herein incorporated by reference. The mRNA transcribed from the human HIF-1 alpha gene can be analyzed for further alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the HIF-1 alpha gene can be used to query such a database to determine whether ESTs representing alternatively spliced mRNAs have been found for a these genes.

A technique called "RNAse protection" can also be used to identify alternatively spliced HIF-1 alpha mRNA. RNAse protection involves translation of a gene sequence into synthetic RNA, which is hybridized to RNA derived from other cells; for example, cells from tissue at or near the site of neovascularization. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced HIF-1 alpha mRNA. In RT-PCR, mRNA from a tissue is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

The mRNA produced from a mutant HIF-1 alpha gene can also be readily identified through the techniques described above for identifying alternative splice forms. As used herein, "mutant" HIF-1 alpha gene or mRNA includes a HIF-1 alpha gene or mRNA which differs in sequence from the HIF-1 alpha mRNA sequences set forth herein. Thus, allelic forms of HIF-1 alpha genes, and the mRNA produced from them, are considered "mutants" for purposes of this invention.

As used herein, a gene or mRNA which is "cognate" to human HIF-1 alpha is a gene or mRNA from another mammalian species which is homologous to human HIF-1 alpha. For example, the cognate HIF-1 alpha mRNA from the rat and mouse are described in GenBank record accession nos. NM_024359 and NM_010431, respectively, the entire disclosure of which is herein incorporated by reference. The rat HIF-1 alpha mRNA sequence is given in SEQ ID NO: 4, and the mouse HIF-1 alpha mRNA sequence is given in SEQ ID NO: 5.

It is understood that human HIF-1 alpha mRNA may contain target sequences in common with their respective alternative splice forms, cognates or mutants. A single siRNA comprising such a common targeting sequence can therefore induce RNAi-mediated degradation of different RNA types which contain the common targeting sequence.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA of the invention can also comprise a 3' overhang. As used herein, a "3' overhang" refers to at least one unpaired nucleotide extending from the 3'-end of a duplexed RNA strand.

Thus in one embodiment, the siRNA of the invention comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA of the invention comprises the sequence AA(N19)TT or NA(N21), where N is any nucleotide. These siRNA comprise approximately 30-70% G/C, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA of the invention comprises the sequence NAR(N17)YNN, where R is a purine (e.g., A or G) and Y is a pyrimidine (e.g., C or U/T). The respective 21-nt sense and antisense strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

The siRNA of the invention can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon. A suitable target sequence in the HIF-1 alpha cDNA sequence is:

```
AACTGGACACAGTGTGTTTGA          SEQ ID NO: 6
```

Thus, an siRNA of the invention targeting this sequence, and which has 3' UU overhangs (overhangs shown in bold) is:

```
5'-aacuaacuggacacagugugu uu-3'    SEQ ID NO: 7
3'-uu uugauugaccugugucacaca-5'    SEQ ID NO: 8
```

An siRNA of the invention targeting this same sequence, but having 3' TT overhangs on each strand (overhangs shown in bold) is:

```
5'-aacuaacuggacacaguguguTT-3'     (SEQ ID NO: 9)
3'-TTuugauugaccugugucacaca-5'     (SEQ ID NO: 10)
```

Exemplary HIF-1 alpha target sequences from which siRNA of the invention can be derived include those in Table 1 and those given in SEQ ID NOS: 39-298.

TABLE 1

HIF-1 Alpha Target Sequences

| target sequence | SEQ ID NO: |
|---|---|
| AACTAACTGGACACAGTGTGT | 11 |
| CGACAAGAAAAAGATAA | 12 |
| AAAGATAAGTTCTGAAC | 13 |
| AGATAAGTTCTGAACGT | 14 |
| GTTCTGAACGTCGAAAA | 15 |
| AAGAAAAGTCTCGAGAT | 16 |
| GAAAAGTCTCGAGATGC | 17 |
| AGTCTCGAGATGCAGCC | 18 |
| GTAAAGAATCTGAAGTT | 19 |
| GAATCTGAAGTTTTTA | 20 |
| GTTTTTTATGAGCTTGC | 21 |
| GGCCTCTGTGATGAGGC | 22 |
| CTTCTGGATGCTGGTGA | 23 |
| AGCACAGATGAATTGCT | 24 |
| AAATGCTTACACACAGAAATG | 25 |
| GAAAAGATAAGTTCTG | 26 |
| AAGATAAGTTCTGAACG | 27 |
| GATAAGTTCTGAACGTC | 28 |
| CGTCGAAAAGAAAAGTC | 29 |
| AGAAAAGTCTCGAGATG | 30 |
| AAGTCTCGAGATGCAGC | 31 |
| GTCTCGAGATGCAGCCA | 32 |
| AGAATCTGAAGTTTTT | 33 |
| TCTGAAGTTTTTATGA | 34 |
| TGTGAGTTCGCATCTTG | 35 |
| ACTTCTGGATGCTGGTG | 36 |
| GATGACATGAAAGCACA | 37 |
| GCACAGATGAATTGCTT | 38 |

The siRNA of the invention can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA of the invention to cells in vivo is discussed in more detail below.

The siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol*, 20: 446-448; Brummelkamp T R et al. (2002), *Science* 296: 550-553; Miyagishi M et al. (2002), *Nat. Biotechnol*. 20: 497-500; Paddison P J et al. (2002), *Genes Dev*. 16: 948-958; Lee N S et al. (2002), *Nat. Biotechnol*. 20: 500-505; and Paul C P et al. (2002), *Nat. Biotechnol*. 20: 505-508, the entire disclosures of which are herein incorporated by reference.

For example, a plasmid can comprise a sense RNA strand coding sequence in operable connection with a polyT termination sequence under the control of a human U6 RNA promoter, and an antisense RNA strand coding sequence in operable connection with a polyT termination sequence under the control of a human U6 RNA promoter.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA of the invention can also be expressed from recombinant viral vectors intracellularly at or near the area of neovascularization in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

The siRNA of the invention can be expressed from a recombinant viral vector either as two separate, complementary nucleic acid molecules, or as a single nucleic acid molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Domburg R (1995), Gene Therap. 2: 301-310; Eglitis M A (1988), Biotechniques 6: 608-614; Miller A D (1990), Hum Gene Therap. 1: 5-14; and Anderson W F (1998), Nature 392: 25-30, the entire disclosures of which are herein incorporated by reference.

Preferred viral vectors are those derived from AV and AAV. In a particularly preferred embodiment, the siRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA of the invention, a method for constructing the recombinant AV vector, and a method for delivering the vector into target cells, are described in Xia H et al. (2002), Nat. Biotech. 20: 1006-1010.

Suitable AAV vectors for expressing the siRNA of the invention, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of HIF-1 alpha protein in the cultured cells can be measured by ELISA or Western blot. A suitable cell culture system for measuring the effect of the present siRNA on target mRNA or protein levels is described in Example 1 below.

The ability of an siRNA to target and cause RNAi-mediated degradation of HIF-1 alpha mRNA can also be evaluated by measuring the levels of VEGF mRNA or protein in cultured cells, as a reduction in HIF-1 alpha expression will also inhibit VEGF expression.

For example, 50% confluent 293 human kidney cells can be incubated with culture medium containing an siRNA (optionally complexed to a transfection reagent such as Mirus Transit TKO transfection reagent) for 48 hours, followed by ELISA or mRNA quantification of either HIF-1 alpha or VEGF. Cells incubated with an siRNA not homologous to the HIF-1 alpha target sequence can be used as controls.

RNAi-mediated degradation of target mRNA by an siRNA containing a given target sequence can also be evaluated with animal models of neovascularization, such as the retinopathy of prematurity ("ROP") or choroidal neovascularization ("CNV") mouse models. For example, areas of neovascularization in an ROP or CNV mouse can be measured before and after administration of an siRNA. A reduction in the areas of neovascularization in these models upon administration of the siRNA indicates the down-regulation of the target mRNA (see Example 2 below).

As discussed above, the siRNA of the invention target and cause the RNAi-mediated degradation of HIF-1 alpha mRNA, or alternative splice forms, mutants or cognates thereof. Degradation of the target mRNA by the present siRNA reduces the production of a functional gene product from the HIF-1 alpha gene. Thus, the invention provides a method of inhibiting expression of HIF-1 alpha in a subject, comprising administering an effective amount of an siRNA of the invention to the subject, such that the target mRNA is degraded. In the practice of the present methods, it is understood that more than one siRNA of the invention can be administered simultaneously to the subject.

Without wishing to be bound by any theory, the products of the HIF-1 alpha gene are believed to be involved in the transcriptional regulation of VEGF. VEGF is in turn required for initiating and maintaining angiogenesis. Thus, the invention also provides a method of inhibiting angiogenesis in a subject by the RNAi-mediated degradation of the target mRNA by an siRNA of the invention.

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit angiogenesis in a subject.

RNAi-mediated degradation of the target mRNA can be detected by measuring levels of the target mRNA or protein in the cells of a subject, using standard techniques for isolating and quantifying mRNA or protein as described above.

Inhibition of angiogenesis can be evaluated by directly measuring the progress of pathogenic or nonpathogenic angiogenesis in a subject; for example, by observing the size of a neovascularized area before and after treatment with the siRNA of the invention. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed by ophthalmoscopy.

Inhibition of angiogenesis can also be inferred through observing a change or reversal in a pathogenic condition associated with the angiogenesis. For example, in ARMD, a slowing, halting or reversal of vision loss indicates an inhibition of angiogenesis in the choroid. For tumors, a slowing, halting or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA of the invention.

It is understood that the siRNA of the invention can degrade the target mRNA (and thus inhibit angiogenesis) in substoichiometric amounts. Without wishing to be bound by any theory, it is believed that the siRNA of the invention induces the RISC to degrade of the target mRNA in a catalytic manner.

Thus, compared to standard anti-angiogenic therapies, significantly less siRNA needs to be delivered at or near the site of neovascularization to have a therapeutic effect.

One skilled in the art can readily determine an effective amount of the siRNA of the invention to be administered to a given subject, by taking into account factors such as the size and weight of the subject; the extent of the neovascularization or disease penetration; the age, health and sex of the subject; the route of administration; and whether the administration is regional or systemic. Generally, an effective amount of the siRNA of the invention comprises an amount which provides an intercellular concentration at or near the neovascularization site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness.

Preferably, an siRNA of the invention is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA of the invention is used to inhibit choroidal neovascularization in age-related macular degeneration.

For treating angiogenic diseases, the siRNA of the invention can administered to a subject in combination with a pharmaceutical agent which is different from the present siRNA. Alternatively, the siRNA of the invention can be administered to a subject in combination with another therapeutic method designed to treat the angiogenic disease. For example, the siRNA of the invention can be administered in combination with therapeutic methods currently employed for treating cancer or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Preferably, the liposomes encapsulating the present siRNA comprise a ligand molecule that can target the liposome to a particular cell or tissue at or near the site of angiogenesis. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), *P.N.A.S., USA*, 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA of the invention are discussed above. Such recombinant plasmids can also be administered to a subject directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to an area of neovascularization in a subject are within the skill in the art.

The siRNA of the invention can be administered to the subject by any means suitable for delivering the siRNA to the cells of the tissue at or near the area of neovascularization. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. For example, the siRNA of the invention can be delivered to retinal pigment epithelial cells in the eye. Preferably, the siRNA is administered topically to the eye, e.g. in liquid or gel form to the lower eye lid or conjunctival cul-de-sac, as is within the skill in the art (see, e.g., Acheampong AA et al, 2002, *Drug Metabol. and Disposition* 30: 421-429, the entire disclosure of which is herein incorporated by reference).

Typically, the siRNA of the invention is administered topically to the eye in volumes of from about 5 microliters to about 75 microliters, for example from about 7 microliters to about 50 microliters, preferably from about 10 microliters to about 30 microliters. The siRNA of the invention is highly soluble in aqueous solutions, It is understood that topical instillation in the eye of siRNA in volumes greater than 75 microliters can result in loss of siRNA from the eye through spillage and drainage. Thus, it is preferable to administer a high concentration of siRNA (e.g., 100-1000 nM) by topical instillation to the eye in volumes of from about 5 microliters to about 75 microliters.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong AA et al, 2002, supra; and Bennett et al. (1996), *Hum. Gene Ther*. 7: 1763-1769 and Ambati J et al., 2002, *Progress in Retinal and Eye Res*. 21: 145-151, the entire disclosures of which are herein incorporated by reference.

The siRNA of the invention can be administered in a single dose or in multiple doses. Where the administration of the siRNA of the invention is by infusion, the infusion can be a single sustained dose or can be delivered by multiple infusions. Injection of the siRNA directly into the tissue is at or near the site of neovascularization preferred. Multiple injections of the siRNA into the tissue at or near the site of neovascularization are particularly preferred.

One skilled in the art can also readily determine an appropriate dosage regimen for administering the siRNA of the invention to a given subject. For example, the siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, more preferably from about seven to about ten weeks. In a preferred dosage regimen, the siRNA is injected at or near the site of neovascularization (e.g., intravitreally) once a week for seven weeks. It is understood that periodic administrations of the siRNA of the invention for an indefinite length of time may be necessary for subjects suffering from a chronic neovascularization disease, such as wet ARMD or diabetic retinopathy.

Where a dosage regimen comprises multiple administrations, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science*, 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups; for example, hydroxypropylcellulose, polyacrylic acid, high-molecular weight polyethylene glycols (e.g., >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

The invention will now be illustrated with the following non-limiting examples. The animal experiments described below were performed using the University of Pennsylvania institutional guidelines for the care and use of animals in research.

EXAMPLE 1

Figure 2:
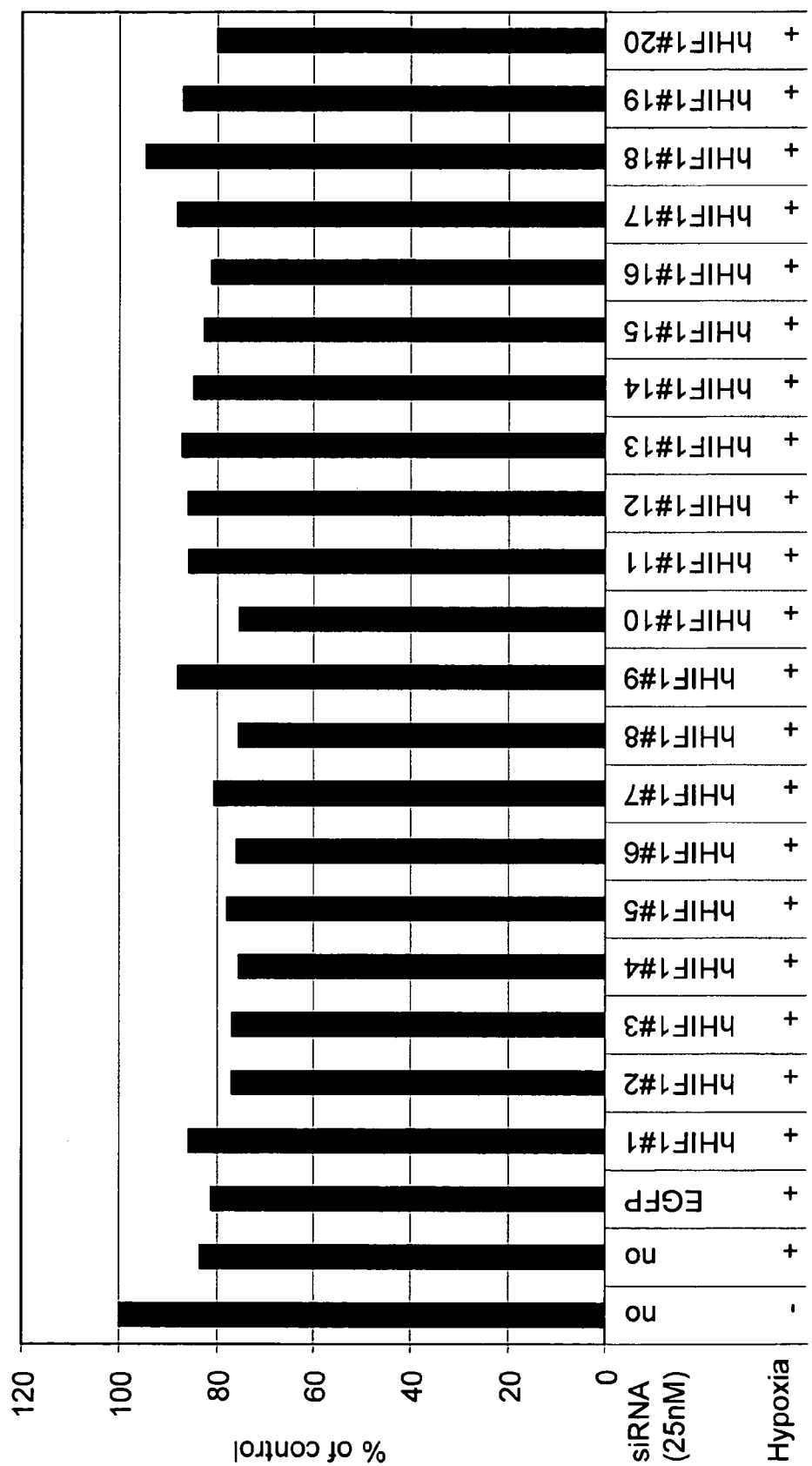
FIG. 2 is a histogram showing cytotoxicity in non-hypoxic ("−") cultured HEK-293 cells treated with no siRNA ("no"), and in hypoxic ("+") cultured HEK-293 cells treated with: no siRNA ("no"); nonspecific siRNA ("EGFP"); or with twenty separate siRNAs targeting human HIF-1 alpha mRNA ("hHIF1#1-20").

Inhibition of Human VEGF Expression in Cultured Human Embryonic Kidney Cells with Anti-HIF-1 Alpha siRNAs Human embryonic kidney 293 (HEK-293) cells were cultured in 24 well plates at 37° C. with 5% $CO_2$ overnight, in standard growth medium. Transfections were performed the following day on experimental and control cells, when the cells were approximately 50% confluent. The experimental cells were transfected with 25 nM human HIF-1 alpha siRNA mixed in calcium phosphate reagent. Control cells were treated with transfection reagent lacking siRNA, or with 25 nM nonspecific siRNA (EGFP1 siRNA) in calcium phosphate transfection reagent. For the experimental cells, twenty different siRNAs targeted to human HIF-1 alpha mRNA were tested. These anti-HIF-1 alpha siRNAs contained the targeting sequences listed in Table 2, and all siRNAs contained 3' TT overhangs on each strand. The "sample #" listed in Table 2 corresponds to the experimental cell sample as indicated in FIGS. 1 and 2.

TABLE 2

Target Sequences for Anti-HIF-1 Alpha siRNAs Tested in HEK-293 Cells

| Target Sequence | SEQ ID NO: | Sample # |
|---|---|---|
| AACTAGCCGAGGAAGAACTAT | 76 | 1 |
| AACTGTCATATATAACACCAA | 117 | 2 |
| AATTACGTTGTGAGTGGTATT | 122 | 3 |
| AAACGCCAAAGCCACTTCGAA | 161 | 4 |
| AAAGTTCACCTGAGCCTAATA | 177 | 5 |
| AAGTTCACCTGAGCCTAATAG | 180 | 6 |

TABLE 2-continued

Target Sequences for Anti-HIF-1
Alpha siRNAs Tested in HEK-293 Cells

| Target Sequence | SEQ ID NO: | Sample # |
|---|---|---|
| AAAGCACAGTTACAGTATTCC | 200 | 7 |
| AAGCACAGTTACAGTATTCCA | 201 | 8 |
| AAAAGACCGTATGGAAGACAT | 212 | 9 |
| AACTACTAGTGCCACATCATC | 222 | 10 |
| AAAGTCGGACAGCCTCACCAA | 223 | 11 |
| AAGTCGGACAGCCTCACCAAA | 224 | 12 |
| AACGTGTTATCTGTCGCTTTG | 237 | 13 |
| AAGCAGTAGGAATTGGAACAT | 255 | 14 |
| AATGGATGAAAGTGGATTACC | 274 | 15 |
| AATGTGAGTTCGCATCTTGAT | 40 | 16 |
| AAGATGACATGAAAGCACAGA | 44 | 17 |
| AACTGGACACAGTGTGTTTGA | 56 | 18 |
| AAATTCCTTTAGATAGCAAGA | 93 | 19 |
| AAACCGGTTGAATCTTCAGAT | 127 | 20 |

At four hours post-transfection, hypoxia was induced in control and experimental HEK-293 cells with desferrioxamine at a final concentration of 200 micromolar. At 48 hours post transfection, the cell culture medium was removed from all wells and a human VEGF ELISA (R & D systems, Minneapolis, Minn.) was performed as described in the Quantikine human VEGF ELISA protocol. ELISA results were read on an AD340 plate reader (Beckman Coulter), and are given in FIG. 1.

As can be seen from FIG. 1, human VEGF protein was upregulated in HEK-293 cells by the desferrioxamine-mediated induction of hypoxia. The hypoxia-induced increase in VEGF protein was reduced in cells transfected with the human anti-HIF-1 alpha siRNAs. Transfections of hypoxic cells with non-specific siRNA (EGFP siRNA) or mock transfection without siRNA had no effect on VEGF protein levels. The anti-HIF-1 alpha siRNAs hHIF1#12, hHIF1#13 and hHIF1#16 reduced VEGF protein expression to levels approaching that of non-hypoxic HEK-293 cells. Anti-HIF-1 alpha siRNA hHIF1#11 reduced VEGF protein expression to below that of non-hypoxic HEK-293 cells.

After the cell culture medium was removed from the control and experimental cells, a cytotoxicity assay was performed as follows. Complete growth medium containing 10% AlamarBlue (Biosource, Camarillo, Calif.) was added to each well, and the cells were incubated at 37° C. with 5% $CO_2$ for 3 hours. Cell proliferation was measured by detecting the color change of medium containing AlamarBlue resulting from cell metabolic activity. Cytotoxicity assay results were read on an AD340 plate reader (Beckman Coulter) and are given in FIG. 2. As can be seen from FIG. 2, none of the twenty anti-HIF-1 alpha siRNAs tested showed significant cytotoxicity in the HEK-293 cells.

After the cytotoxicity assay was performed, the growth medium in each well was completely removed, and RNA extractions from the HEK-293 cells were performed with the RNAqueous RNA isolation kit (Ambion, Austin, Tex.) according to the manufacturer's instructions. The levels of human HIF-1 alpha and VEGF mRNA in the cells were measured by quantitative reverse transcription-polymerase chain reaction (RT-PCR), using the level of human glyceraldehyde-3-phosphate dehydrogenase (GAPDH) mRNA as an internal standard.

The RT-PCR study showed that hypoxia increased the mRNA levels of human VEGF relative to VEGF mRNA expression in non-hypoxic cells. The VEGF mRNA levels in hypoxic cells were reduced by transfection with anti-HIF-1 alpha siRNAs. Transfection of hypoxic cells with non-specific siRNA (EGFP siRNA) or mock transfection with no siRNA did not reduce VEGF mRNA levels. Thus, the introduction of anti-HIF-1 alpha siRNAs into the HIK-293 cells induced the destruction of the VEGF mRNA, as compared to cells transfected with non-specific siRNA or no siRNA. The destruction of VEGF mRNA induced by the anti-HIF-1 alpha siRNAs correlated with the reduction in VEGF protein production shown in FIG. 1.

EXAMPLE 2

In Vivo Inhibition of Angiogenesis with Anti-HIF-1 Alpha siRNA in a Mouse Model of Choroidal Neovascularization Adult (8-15 week old) female C57B1/6 mice (n=7) were anesthetized with avertin (2,2,2-tribromoethanol) and their pupils were dilated with 1% tropicamide. Laser photocoagulation was performed bilaterally using a diode laser photocoagulator (IRIS Medical, Mountain View, Calif.) and a slit lamp system with a cover slip as a contact lens. Laser photocoagulation (140 mW; 75 micron spot size; 0.1 s duration) was applied to the 9, 12 and 3 o'clock positions in both eyes at 2 to 3 disk diameters from the optic nerve. Since the rupture of Bruch's membrane is necessary to create significant choroidal neovascularization (CNV), bubble formation at the time of photocoagulation was used as an indication of the rupture of Bruch's membrane. Laser burns that did not induce a rupture in Bruch's membrane were excluded from the study.

Immediately after laser treatment, an siRNA targeted to mouse HIF-1 alpha mRNA was delivered to both eyes of each animal in the test group by intravitreal injection. Control animals received intravitreal injection of carrier only.

The target sequence of the mouse anti-HIF-1 alpha mRNA was AACTAACTGGACACAGTGTGT (SEQ ID NO: 297), and the siRNA used was:

| | |
|---|---|
| 5'-cuaacuggacacaguguguTT-3' | (SEQ ID NO: 298) |
| 3' TTgauugaccugugucacaca5' | (SEQ ID NO: 299) |

Twelve days after laser photocoagulation, the animals were perfused with high molecular weight dextran-fluorescein (Molecular Probes, Eugene, Oreg.) to label the retinal/choroidal vasculature, and the eyes were harvested. The area of each CNV was measured in choroidal flat mount preparations.

To prepare choroidal flat mounts, the anterior chamber was removed and the retina was extracted with the vitreous, leaving the eyecup. Relaxing incisions were made on the eye cup and the choroid was flattened onto a slide. Using a Leica DMR microscope (Wetzlar, Germany) equipped with epifluorescence illumination, a masked investigator identified lesions in the dextran-fluorescein-perfused flat mount preparations as circular fluorescent (fluorescein positive) areas corresponding to the area previously exposed to the laser light.

Images of the lesions were captured using a black and white Hamamatsu CCD camera (Hamamatsu Photonics, Bridgewater, N.J.) coupled to a Apple Macintosh G4 computer (Cupertino, Calif.) equipped with OpenLab 2.2 software. Images for calibration were obtained from a slide with a grating of known size. The hyperfluorescent fluorescein-dextran labeled blood vessels within the area of the laser burn were selected as "region of interest" (ROI) using Openlab software, and this software was used to calculate the area ($\mu m^2$) occupied by the white pixels in the ROIs. The ROIs were selected after collecting the images under identical integration settings by using the Openlab "magic wand" tool to identify pixels in the laser burn site at a range of 2000-4090 intensity units, as defined within the Openlab software. The intensity units which were selected represented levels measured in normal fluorescein-perfused vasculature. For reference, the intensity of background, non-fluorescent areas was <450 intensity units.

The ROIs were generally well-circumscribed by a region lacking fluorescence. After measuring the areas of CNV, images were colorized in Openlab by applying an intensity ramp at 515 nanometers (the wavelength at which the image data were captured), using the "apply wavelength" function in the Openlab software. This intensity ramp was applied to all of the pixels in the image, and made the whitest pixels the brightest green color. The images were then exported to Adobe Photoshop software for presentation purposes. Situations in which there was no evidence of a laser burn after bright field analysis of choroidal flatmounts were excluded.

Figure 3:
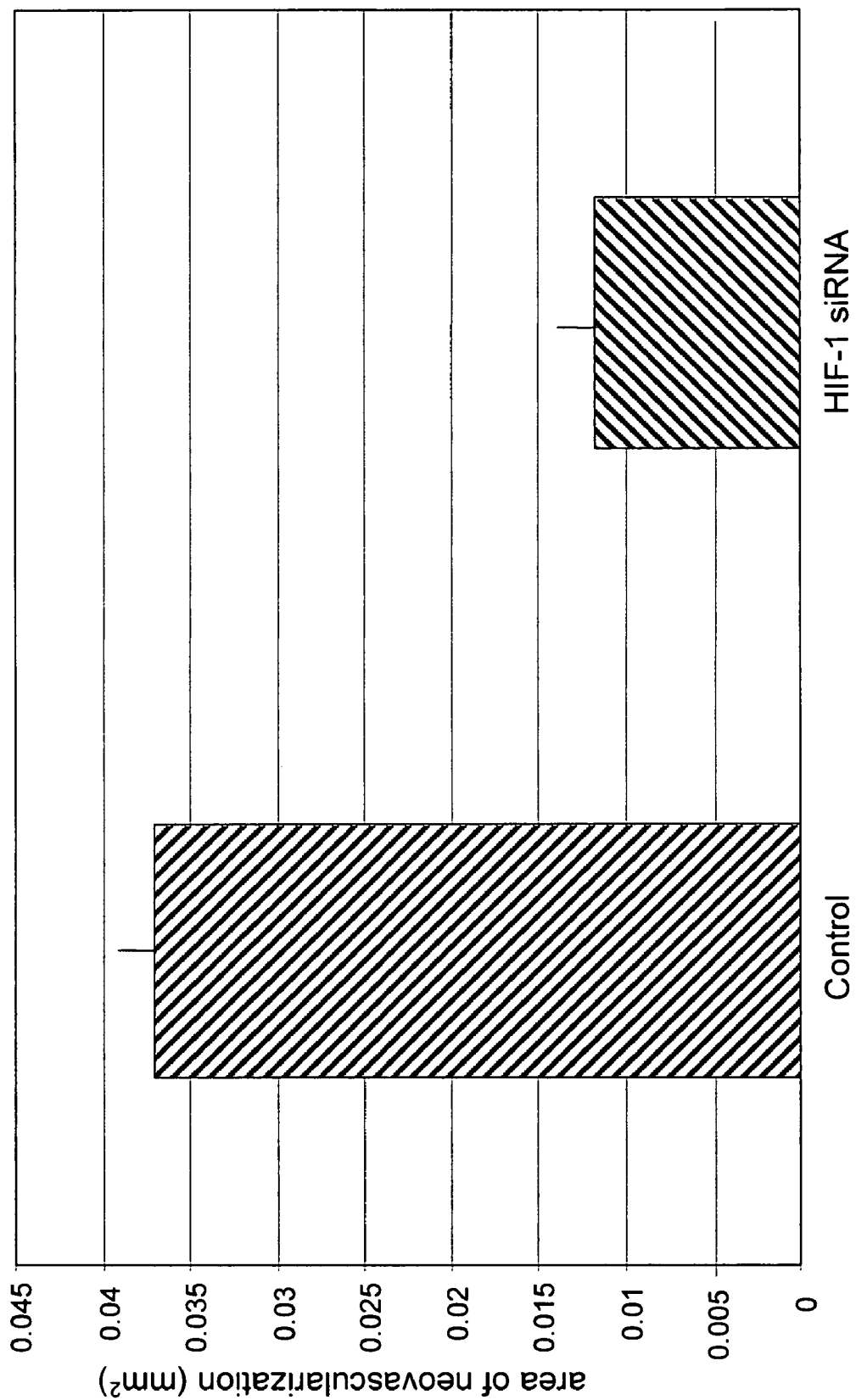
FIG. 3 is a histogram showing the area of choroidal neovascularization in mm², in eyes from control mice ("control") and mice treated with anti-HIF-1 alpha siRNA ("HIF-1 siRNA").

Statistical analysis of the results was performed using a one-tailed distribution, two sample unequal variance Student's t-test. There was a statistically significant reduction in the CNV area (P=0.000354) between the anti-HIF-1 alpha siRNA treated animals and the control lasered animals, indicating a substantial reduction in angiogenesis in the animals receiving the anti-HIF-1 alpha siRNA. The results are presented in FIG. 3.

We claim:

1. A method of inhibiting expression of human HIF-1 alpha mRNA comprising administering to a subject an effective amount of an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human HIF-1 alpha mRNA such that human HIF-1 alpha mRNA is degraded and wherein said target sequence is SEQ ID NO. 223.

2. The method of claim 1, wherein the subject is a human being.

3. The method of claim 1, wherein expression of human HIF-1 alpha mRNA is inhibited in one or both eyes of the subject.

4. The method of claim 1, wherein expression of human HIF-1 alpha mRNA is inhibited in retinal pigment epithelial cells of the subject.

5. The method of claim 1, wherein the effective amount of the siRNA is an amount which provides an intercellular concentration at or near a neovascularization site of from about 1 nM to about 100 nM.

6. The method of claim 1, wherein the siRNA is administered in conjunction with a delivery reagent.

7. The method of claim 6, wherein the delivery agent is selected from the group consisting of lipofectin, lipofectamine, cellfectin, polycations, and liposomes.

8. The method claim 1, wherein the siRNA is delivered at or near a site of angiogenesis.

9. The method of claim 1, wherein the siRNA is expressed from a recombinant plasmid.

10. The method of claim 1, wherein the siRNA is expressed from a recombinant viral vector.

11. The method of claim 10, wherein the recombinant viral vector comprises an adenoviral vector, an adeno-associated viral vector, a lentiviral vector, a retroviral vector, or a herpes virus vector.

12. The method of claim 11, wherein the recombinant viral vector is pseudotyped with vesicular stomatitis virus, rabies virus, Ebola virus, or Mokola virus.

13. The method of claim 10, wherein the recombinant viral vector comprises an adeno-associated viral vector.

14. The method of claim 1, wherein the siRNA is administered by an enteral administration route.

15. The method of claim 14, wherein the enteral administration route is selected from the group consisting of oral, rectal, and intranasal.

16. The method of claim 1, wherein the siRNA is administered by a parenteral administration route.

17. The method of claim 16, wherein the parenteral administration route is selected from the group consisting of intravascular administration, peri- and intra-tissue administration, subcutaneous injection or deposition, subcutaneous infusion, intraocular administration, and direct application at or near a site of neovascularization.

18. The method of claim 17, wherein the intravascular administration is selected from the group consisting of intravenous bolus injection, intravenous infusion, intra-arterial bolus injection, intra-arterial infusion and catheter instillation into the vasculature.

19. The method of claim 17, wherein the peri- and intra-tissue injection comprises peri-tumoral injection or intra-tumoral injection.

20. The method of claim 17, wherein the intraocular administration comprises intravitreal, intraretinal, subretinal, subtenon, peri- and retro-orbital, trans-corneal or trans-scleral administration.

21. The method of claim 17, wherein the direct application at or near the site of neovascularization comprises application by catheter, corneal pellet, eye dropper, suppository, an implant comprising a porous material, an implant comprising a non-porous material, or an implant comprising a gelatinous material.

22. The method of claim 17, wherein the site of neovascularization is in the eye, and the direct application at or near the site of neovascularization comprises application by an ocular implant.

23. The method of claim 22, wherein the ocular implant is biodegradable.

24. A method of inhibiting angiogenesis in a subject, comprising:
   administering to a subject an effective amount of an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human HIF-1 alpha mRNA; and
   degrading the HIF-1 alpha mRNA in the subject, and wherein said target sequence is SEQ ID NO. 223.

25. The method of claim 24, wherein the angiogenesis is characteristic of a disease.

26. The method of claim 24, wherein the angiogenesis is associated with production of fatty tissues or cholesterol production.

27. The method of claim 24, wherein the angiogenesis comprises endometrial neovascularization.

28. The method of claim 24, wherein the angiogenesis is inhibited in one or both eyes of the subject.

29. A method of treating an angiogenic disease in a subject, comprising:
   administering to a subject an effective amount of an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human HIF-1 alpha mRNA; and
   degrading the human HIF-1 alpha mRNA such that angiogenesis associated with the angiogenic disease is inhibited, and wherein said target sequence is SEQ ID NO. 223.

30. The method of claim 29, wherein the angiogenic disease comprises a tumor associated with a cancer.

31. The method of claim 30, wherein the cancer is selected from the group consisting of breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, lymphoma, and blood cancer.

32. The method of claim 29, wherein the angiogenic disease is selected from the group consisting of diabetic retinopathy, age-related macular degeneration, and inflammatory diseases.

33. The method of claim 32, wherein the inflammatory disease is psoriasis or rheumatoid arthritis.

34. The method of claim 32, wherein the angiogenic disease is age-related macular degeneration.

35. The method of claim 29, wherein the siRNA is administered in combination with a pharmaceutical agent for treating the angiogenic disease, which pharmaceutical agent is different from the siRNA.

36. The method of claim 35, wherein the angiogenic disease is cancer, and the pharmaceutical agent comprises a chemotherapeutic agent.

37. The method of claim 35, wherein the pharmaceutical agent is selected from the group consisting of cisplatin, carboplatin, cyclophosphamide, 5-fluorouracil, adriamycin, daunorubicin, and tamoxifen.

38. The method of claim 29, wherein the siRNA is administered to a subject in combination with another therapeutic method designed to treat the angiogenic disease.

39. The method of claim 38, wherein the angiogenic disease is cancer, and the siRNA is administered in combination with radiation therapy, chemotherapy or surgery.

* * * * *